United States Patent [19]

Kilbourn et al.

[11] Patent Number: 5,374,651

[45] Date of Patent: Dec. 20, 1994

[54] METHODS AND COMPOSITIONS FOR THE TREATMENT OF HYPOTENSION WITH ARGININE FREE ESSENTIAL AND ESSENTIAL AMINO ACIDS AND ARGININE DERIVATIVES

[75] Inventors: Robert G. Kilbourn, Houston, Tex.; Owen W. Griffith, Milwaukee, Wis.; Steven S. Gross, New York, N.Y.

[73] Assignee: Board of Regents, The University of Texas System, Austin, Tex.

[21] Appl. No.: 902,653

[22] Filed: Jun. 23, 1992

Related U.S. Application Data

[63] Continuation-in-part of Ser. No. 767,265, Sep. 27, 1991, Pat. No. 5,286,739.

[51] Int. Cl.$^5$ .......................................... A61K 31/195
[52] U.S. Cl. ................................. 514/400; 514/564; 514/565; 514/561; 514/567; 514/419
[58] Field of Search .................... 514/565, 12, 561, 19, 514/419, 423

[56] References Cited

U.S. PATENT DOCUMENTS

| | | | |
|---|---|---|---|
| 4,100,160 | 7/1978 | Walser et al. | 424/274 |
| 4,282,217 | 8/1981 | Baglioni et al. | 424/240 |
| 4,426,378 | 1/1984 | Holaday | 424/177 |
| 4,734,438 | 3/1988 | Macri | 514/653 |
| 4,859,452 | 8/1989 | Ajani et al. | 424/10 |
| 4,988,724 | 1/1991 | Ajani et al. | 514/399 |
| 5,006,559 | 4/1991 | Askanazi et al. | 514/561 |
| 5,028,627 | 7/1991 | Kilbourn et al. | 514/565 |
| 5,036,052 | 7/1991 | Ozeki et al. | 514/19 |
| 5,059,712 | 10/1991 | Griffith | 562/560 |
| 5,132,453 | 7/1992 | Griffith | 562/560 |
| 5,158,883 | 10/1992 | Griffith | 435/240.2 |
| 5,196,195 | 3/1993 | Griffith | 424/94.6 |
| 5,216,025 | 6/1993 | Gross et al. | 514/565 |
| 5,286,739 | 2/1994 | Kilbourn et al. | 514/400 |
| 5,296,466 | 3/1994 | Kilbourn et al. | 514/400 |

FOREIGN PATENT DOCUMENTS

| | | |
|---|---|---|
| 0295166A1 | 12/1988 | European Pat. Off. |
| 0312612A1 | 4/1989 | European Pat. Off. |
| 0318446A1 | 5/1989 | European Pat. Off. |
| 0405295A2 | 1/1991 | European Pat. Off. |
| 2516027 | 10/1975 | Germany |
| 2516027A1 | 10/1975 | Germany |
| WO91/04024 | 9/1990 | WIPO ................ A61K 31/195 |
| WO91/84023 | 4/1991 | WIPO |

OTHER PUBLICATIONS

PCT/US92/08227 International Preliminary Examination Report mailed Dec. 3, 1993.

Martin et al., "Selective Blockade of Endothelium-Dependent and Glyceryl Trinitrate-Induced Relaxation by Hemoglobin and by Methylene Blue in the Rabbit Aorta," *The Journal of Pharmacology and Experimental Therapeutics*, 232(3):708–716, 1985, published in USA.

Buga et al., "Endothelium-Derived Nitric Oxide Relaxes Nonvascular Smooth Muscle," *European Journal of Pharmacology*, 161:61–72, 1989, published in Europe.

Torti et al., "A Macrophage Factor Inhibits Adipocyte Gene Expression: An in Vitro Model of Cachexia," *Scinece*, 229:867–871, 1985, published in USA.

Old, Lloyd J., "Tumor Necrosis Factor (TNF)," 230:630–632, 1985, published in USA.

Yoshida and Kasama, "Biotransformation of Nitric Oxide," *Environmental Health Perspectives*, 73:201–206, 1987, published in USA.

Reif and Simmons, "Nitric Oxide Mediates Iron Release from Ferritin," *Archives of Biochemistry and Biophysics*, 283(2):537–541, 1990, published in USA.

Kruszyna et al., "Nitrite Conversion to Nitric Oxide in Red Cells and Its Stabilization as a Nitrosylated Valency Hybrid of Hemoblobin," *The Journal of Pharmacology and Experimental Therapeutics*, 241(1):307–313, 1987, published in USA.

Kosaka et al., "The Interaction Between Nitrogen Oxides and Hemoglobin and Endothelium-Derived Relaxing Factor," *Free Radical Biology and Medicine*, 7:653–658, 1989, published in USA.

Chevion et al., "Iron-Nitrosyl Bond Configuration in Nitrosyl-Hemoproteins: A Comparative EPR Study of Hemoglobin A and Hemoglobin Kansas," *Israel Journal of Chemistry*, 15:311–317, 1976, published in Israel.

Collier and Vallance, "Second Messenger Role for NO Widens to Nervous and Immune Systems," *Trends in Pharmacological Sciences Including Toxicological Sci-*

*ences*, Elseview Science Publishers, Ltd., front page and pp. 428–431, 1989, published in United Kingdom.

Ignarro et al., "Endothelium–Derived Relaxing Factor Produced and Released from Artery and Vein is Nitric Oxide," *Proc. Natl. Acad. Sci. USA*, 84:9265–9269, 1987, published in USA.

Murray et al., "Stailization and Partial Characterization of Endothelium–Derived Relaxing Factor from Cultured Bovine Aortic Endothelial Cells," *Biochemical and Biophysical Research Communications*, 141(2):689–696, 1986, published in USA.

Marletta, Michael A., "Nitric Oxide: Biosynthesis and Biological Significance," name of publication unknown, Elseview Science Publishers, Ltd., pp. 448–493, 1989, published in United Kingdom.

Sakuma, I. et al., (1988) "Identification of Arginine as a Precursor of Endothelium–Derived Relaxing Factor," *Proc. Natl. Acad. Sci. USA*, 85:8664–8667, published in U.S.A.

Abstract entitled "Nitric Oxide Damages DNA in Bacteria," *Chem. and Engineering News*, Nov. 18, 1991, published in U.S.A.

Wink et al., (1991) "DNA Deaminating Ability and Genotoxicity of Nitric Oxide and its Progenitors," *Scinece*, 254:1001–1003, published in U.S.A.

Kilbourn et al., (1984) "Activated Macrophages Secrets a Soluble Factor that Inhibits Mitochondrial Respiration of Tumor Cells," *J. Immunology*, 133:2577–2581, published in U.S.A.

Kilbourn et al., (1990) "Reversal of Endotoxin-Mediated Shock by $N^G$–Methyl–L–Arginine, an Inhibitor of Nitric Oxide Synthesis," *Biochem. and Biophys. Res. Commun.*, 172:1132–1138, published in U.S.A.

Kilbourn, R. G., et al., (1990) "$N^G$–Methyl–L–Arginine Inhibits Tumor Necrosis Factor–Induced Hypotension: Implications for the Involvement of Nitric Oxide," *Proc. Natl. Acad. Sci. USA*, 87:3629–3632, published in U.S.A.

Schmidt et al., (1992) "Insulin Secretion from Pancreatic B Cells Caused by L–Arginine–Derived Nitrogen Oxides," *Scinece*, 255:721–723, published in U.S.A.

Turan, A. et al., (1975) "Removal of the Nitro Group from Nitroarginine and Nitroarginine Peptides," *Acta Chimica Academiae Scientiarum Hungaricae, Tomas*, 85:327–332, published in Europe.

Iyengar, R. et al., (1987) "Macrophage Synthesis of Nitrite, Nitrate, and N–Nitrosamines: Precursors and Role of the Respiratory Burst," *Proc. Natl. Acad. Sci. USA*, 84:6369–6373, published in U.S.A.

Stuehr et al., (1987) "Induction of Nitrite/Nitrate Synthesis in Murine Macrophages by BCG Infection, Lymphokines, or Interferon–$\gamma^1$" *J. Immunology*, 139:518–525, published in U.S.A.

Marletta et al., (1988) "Macrophage Oxidation of L–Arginine to Nitrite and Nitrate: Nitric Oxide Is an Intermediate," *Biochemistry*, 27:8706–8711, published in U.S.A.

Palmer, R. M. J. et al., (1988) "Vascular Endothelial Cells Synthesize Nitric Oxide from L–Arginine," *Nature*, 333:664–666, published in the United Kingdom.

Palmer, R. M. J. et al., (1988) "L–Arginine is the Physiological Precursor for the Formation of Nitric Oxide in Endothelium–Dependent Relaxation," *Biochem. Biophys. Res. Commun.*, 153:1251–1256, published in U.S.A.

Schmidt et al., (1988) "Arginine is a Physiological Precursor of Endothelium–Derived Nitric Oxide," *European J. Pharmacology*, 154:213–216, published in Europe.

Aisaka et al., (1989) "$N^G$–Methylarginine, An Inhibitor of Endothelium–Derived Nitric Oxide Synthesis, Is a Potent Pressor Agent in the Guinea Pig: Does Nitric Oxide Regulate Blood Pressure in Vivo?" *Biochem. Biophys. Res. Commun.*, 160:881–886, published in U.S.A.

Rees, D. D. et al., (1989) "Role of Endothelium–Derived Nitric Oxide in the Regulation of Blood Pressure," *Proc. Natl. Acad. Sci. USA*, 86:3375–3378, published in U.S.A.

Stuehr, D. J., et al., (1989) "Activated Murine Macrophages Secrete a Metabolite of Arginine with the Bioactivity of Endothelium–Derived Relaxing Factor and the Chemical Reactivity of Nitric Oxide," *J. Exp. Med.*, 169:1011–1020, published in U.S.A.

Stuehr, D. J. et al., (1989) "Synthesis of Nitrogen Oxides from L–Arginine by Macrophage Cytosol: Requirement for Inducible and Constitutive Components," *Biochem. Biophys. Res. Commun.*, 161:420–426, published in U.S.A.

Piguet et al., (1989) "Tumor Necrosis Factor/Cachectin Plays a Key Role in Bleomycin–Induced Pneumopathy and Fibrosis," *J. Exp. Med.*, 170:655–663, published in U.S.A.

Kilbourn et al., (1990) "Endothelial Cell Production of Nitrogen Oxides in Response to Interferon γ in Combination with Tumor Necrosis Factor, Interleukin-1, or Endotoxin," *J. Natl. Cancer Institute*, 82:772–776, published in U.S.A.

Gennaro, Alfonso R., Editor, and Chairman of the Editorial Board (1990) "Sympathomimetic Drugs", *Remington's -Pharmaceutical Sciences*, 18th Edition, p. 877, published in U.S.A.

Windholz, Martha, Editor, (1983) "Dobutamine," *The Merck Index, An Encyclopedia of Chemicals, Drugs, an Biologicals*, Tenth Edition, 3407, p. 495, published in U.S.A.

Klabunde and Ritger, (1991) "$N^G$-Monomethyl-L-Arginine (NMA) Restores Arterial Blood Pressure but Reduces Cardiac Output in a Canine Model of Endotoxic Shock," *Biochemical and Biophysical Research Communications*, 178(3):1135–1140, published in U.S.A.

Klabunde, et al., (1991) "Cardiovascular Actions of Inhibitors of Endothelium-Derived Relaxing Factor (Nitric Oxide) Formation/Release in Anesthetized Dogs," *European Journal of Pharmacology*, 199:51–59, published in the Netherlands.

Vincent, et al., (1990) "Dobutamine Administration in Septic Shock: Addition to a Standard Protocol," *Critical Care Medicine*, 18(7):689–693, published in U.S.A.

Vincent et al., (1990) "Septic Shock: Particular Type of Acute Circulatory Failure," *Critical Care Medicine*, 18(1):S70–S74, published in U.S.A.

Shoemaker et al., (1990) "Therapy of Shock Based on Pathophysiology, Monitoring, and Outcome Prdiction," *Critical Care Medicine*, 18(1):S19–S25, published in U.S.A.

Schremmer et al., (1990) "Heart Failure in Septic Shock: Effects of Inotropic Support," *Critical Care Medicine*, 18(1):S49–S55, published in U.S.A.

Carter et al., (1990) "Purification, Cloning, Expression and Biological Characterization of An Interleukin-1 Receptor Antagonist Protein," *Nature*, 344:633–638, published in United Kingdom.

Hannum et al., (1990) "Interleukin-1 Receptor Antagonist Activity of a Human Interleukin-1 Inhibitor," *Nature*, 343:336–340, published in United Kingdom.

Eisenberg et al., (1990) "Primary Structure and Functional Expression from Complementary DNA of a Human Interleukin-1 Receptor Antagonist," *Nature*, 343:341–346, published in United Kingdom.

Teng et al., (1985) "Protection Against Gram-Negative Bacteremia and Endotoxemia with Human Monoclonal IgM Antibodies," *Proc. Natl. Acad. Sci. USA*, 82:1790–1794, published in U.S.A.

Bone, Roger C., (1991) "A Critical Evaluation of New Agents for the Treatment of Sepsis," *JAMA*, 266(12):1686–1691, published in U.S.A.

Ziegler et al., (1991) "Treatment of Gram-Negative Bacteremia and Septic Shock with HA–1A Human Monoclonal Antibody Against Endotoxin," *The New England Journal of Medicine*, 324(7):429–436, published in U.S.A.

Lancaster, Jack R., (1992) "Nitric Oxide in Cells: This Simple Molecule Plays Janus-Faced Roles in the Body, Acting As Both Messenger and Destroyer," *American Scientist*, 80:248–257, published in U.S.A.

Gross et al., (1990) "Macrophage and Endothelial Cell Nitric Oxide Synthesis: Cell-Type Selective Inhibition by $N^G$-Aminoarginine, $N^G$-Nitroarginine and $N^G$-Methylarginine," *Biochemical and Biophysical Research Communications*, 170(1):96–103, published in U.S.A.

Wakabayashi et al., (1991) "A Specific Receptor Antagonist for Interluekin 1 Prevents Escherichia coli-Induced Shock in Rabbits," *The FASEB Journal*, 5:338–343, published in U.S.A.

Baumgartner et al., (1990) "Association Between Protective Efficacy of Anti-Lipopolysaccharide (LPS) Antibodies and Suppression of LPS-Induced Tumor Necrosis Factor α and Interleukin 6," *J. Exp. Med.*, 171:889–896, published in U.S.A.

Calandra et al., (1991) "Anti-14 Lipopolysaccharide and Anti-Tumor Necrosis Factor/Cachectin Antibodies for the Treatment of Gram-Negative Bacteremia and Septic Shock," *Bacterial Endotoxins: Cytokine Mediators and New Therapies for Sepsis*, pp. 141–159, published by Wiley-Liss, Inc., place of publication unknown.

Calandra et al., (1988) "Treatment of Gram-Negative Septic Shock with Human IgG Antibody to *Escherichia coli* J5: A prospective, Double-Blind, Randomized Trial," *The Journal of Infectious Diseases*, 158(2):312–319, published in U.S.A.

Opal et al., (1991) "Efficacy of Antilipopolysaccharide and Anti-Tumor Necrosis Factor Monoclonal Antibodies in a Neutropenic Rat Model of Pseudomonas Sepsis," *J. Clin. Invest.*, 88:885–890, published in U.S.A.

Wolff, Sheldon M., (1991) "Monoclonal Antibodies and the Treatment of Gram–Negative Bacteremia and Shock," *The New England Journal of Medicine*, pp. 486–488, published in U.S.A.

Kilbourn et al., (1992) "Overproduction of Nitric Oxide in Cytokine–Mediated and Septic Shock," *Journal of the National Cancer Institute*, 84(11):827–831, published in U.S.A.

Natanson et al., (1989) "Endotoxin and Tumor Necrosis Factor Challenges in Dogs Simulate the Cardiovascular Profile of Human Septic Shock," *The Journal of Experimental Medicine*, 169:823–832, published in U.S.A.

Hibbs et al., (1988) "Nitric Oxide: A Cytotoxic Activated Macrophage Effector Molecule," *Biochemical and Biophysical Research Communications*, 157(1):87–94, published in U.S.A.

Palmer et al., (1987) "Nitric Oxide Release Accounts for the Biological Activity of Endothelium–Derived Relaxing Factor," *Nature*, 327:524–526, published in United Kingdom.

Moncada et al., (1986) "Generation of Prostacycline and Endothelium–Derived Relaxing Factor from Endothelial Cells," IN: Golles, G., Legran J. Y., and Nurden A. eds., *Biology and Pathology of Platelets–Vessel Wall Interactions*, pp. 289–304, published in London.

Vallance et al., (1989) "Effects of Endothelium–Derived Nitric Oxide on Peripheral Arteriolar Tone in Man," *Lancet*, 28:997–999, published in Great Britain.

Bone, Roger C., (1991) "The Pathogenesis of Spesis," *Ann. Int. Med.* 115:457–469, published in USA.

Glauser, M. P. et al., (1991) "Septic Shock: Pathogenesis," *The Lancet*, 338:732–736, published in United Kingdom.

Johnston, J., (1991) "Molecular Science Sets Its Sights on Septic Shock," *J. NIH Res.* 3:61–65, published in USA.

Moncada, S. and E. A. Higgs, (1991) "Endogenous Nitric Oxide: Physiology, Pathology, and Clinical Relevance," *Eur. J. Clin. Invest.* 21:361–374, published in Europe.

Moncada, S., et al., (1991) "The L–Arginine: Nitric Oxide Pathway," *J. Cardiovascular Pharm.* 7(Suppl. 3):S1–S9, published in USA.

Moncada, S., et al., (1991) "Nitric Oxide: Physiology, Pathophysiology, and Pharmacology," *Pharmacological Reviews* 43(2):109–142, published in USA.

Parratt, J. R., and J. C. Stoclet, (1991) "Possible Role of Nitric Oxide in Refractory Hypotension Associated with Sepsis and Endotoxaemia and with Multiple Organ Failure," *Applied Cardiopulmonary Pathophysiology* 4:143–149, published in the Netherlands.

Snell, R. J., and J. E. Parrillo, (1991) "Cardiovascular Dysfunction in Septic Shock," *Chest* 99(4):1000–1009, published in USA.

Wang et al. (1991), "Nitric Oxide Hemoglobin in Mice and Rats in Endotoxic Shock," *Life Sciences* 49:PL–5-5–60, 1991, Published in USA.

Exley et al., (1990), "Monoclonal Antibody to TNF in Severe Septic Shock," *The Lancet*, 335:1275–1277, published in U.S.A.

Starnes et al., (1988), "Tumor Necrosis Factor and the Acute Metabolic Response to Tissue Injury in Man," *J. Clinical Invest.*, 82:1321–1325, Abstract from Dialog Search Report, published in USA.

Nathan, C. F. and Stuehr, D. J., (1990), "Does Endothelium–Derived Nitric Oxide Have a Role in Cytokine–Induced Hypotension?" *J. Natl. Cancer Inst.*, 82(9):726–728, Abstract from Dialog Search Report, published in USA.

Fukuto et al., (1990), "$N^G$–Amino-L-Arginine: A New Potent Antagonist of L-Arginine–Mediated Endothelium–Dependent Relaxation," *Biochem. Biophys. Res. Comm.*, 168(2):458–465, published in USA.

Hibbs et al., (1987), "L-Arginine is Required for Expression of the Activated Macrophage Effector Mechanism Causing Selective Metabolic Inhibition in Targt Cells," *J. of Immunol.*, 138(2):550–565, published in USA.

Lambert et al. (1991), "Nitric Oxide Synthesis in the CNS, Endothelium and Macrophages Differs in its Sensitivity to Inhibition by Arginine Analogues," *Life Sciences*, 48:69–75, published in USA.

Billiar et al., (1990), "Modulation of Nitrogen Oxide Synthesis In Vivo: $N^G$–Monomethyl-L-Arginine Inhibits Endotoxin–Induced Nitrite/Nitrate Biosynthesis While Promoting Hepatic Damage," *Journal of Leukocyte Biology*, 48:565–569, published in U.S.A.

Nava et al., (1991), "Inhibition of Nitric Oxide Synthesis in Septic Shock: How Much Is Beneficial?" *The Lancet,* 338:1555–1557, published in Great Britain.

Calandra et al., (1990), "Prognostic Values of Tumor Necrosis Factor/Cachectin, Interleukin–1, Interferon-α, and Interferon-γ in the Serum of Patients with Septic Shock," *The Journal of Infectious Diseases,* 161:982–987, published in USA.

Corbin, James L., (1974), "$N^G$-Methylated Arginines; A Convenient Preparation of $N^G$-Methylarginine," *Analytical Biochemistry,* 57:310–312, published in USA.

Ohlsson et al., (1990), "Interleukin–1 Receptor Antagonist Reduces Mortality from Endotoxin Shock," *Nature,* 348:550–552, published in Great Britain.

*Primary Examiner*—Marianne M. Cintins
*Assistant Examiner*—T. J. Criapres
*Attorney, Agent, or Firm*—Arnold, White & Durkee

[57] ABSTRACT

Methods and compositions for treating and inhibiting hypotension are provided. A therapeutic regimen useful in the present invention includes an arginine-free parenteral formulation administered concurrently with or followed by an arginine analog. The combination therapy provides an augmentation of the anti-hypotensive effect found by the present inventors with arginine analogs, such as $N^\omega$-methyl-L-arginine, $N^\omega$-amino-L-arginine or $N^\omega$-nitro-L-arginine. These arginine analogs, otherwise described as nitric oxide synthase inhibitors, provide for a decrease in nitric oxide concentrations, and are demonstrated to elicit an increase in blood pressure in vivo, particularly in animals with cytokine and/or endotoxin induced hypotension. The parenteral formulation of the therapeutic regimen and methods of the invention are arginine-free and provide a decrease in plasma arginine levels. Reduced plasma and tissue levels of arginine in the animal function to augment the hypertensive action of arginine analogs to be administered concurrently or subsequent to administration of the parenteral formulation. This method provides a regiment for treating and/or inhibiting hypotension attendant a variety of conditions, including chemotherapeutic agent therapy (i.e., IFN, TNF), septic shock, trauma, exposure to endotoxins or cytokines, or other condition in which hypotension is attendant. The arginine-free formulations may also include ornithine, citrulline, or both.

46 Claims, 7 Drawing Sheets

METHODS AND COMPOSITIONS FOR THE TREATMENT OF HYPOTENSION WITH ARGININE FREE ESSENTIAL AND ESSENTIAL AMINO ACIDS AND ARGININE DERIVATIVES

The government has rights in the present invention as research relevant to the development thereof was funded by NIH grant #DK37116.

The present application is a continuation-in-part of U.S. Ser. No. 07/767,265, filed Sep. 27, 1991, now U.S. Pat. No. 5,286,739, issued Feb. 15, 1994.

BACKGROUND OF THE INVENTION

1. Field of the Invention

The present invention relates to the field of methods and compositions for the treatment of hypotension. The invention also relates to the field of combination therapeutic regimens particularly those which include a regimen of a particularly tailored parenteral formulation. The present invention also relates to the field of nitric oxide inhibitors as therapeutic agents in a combination therapeutic regimen.

2. Background of the Related Art

Hypotension, or low blood pressure, is a complicating and often life-threatening condition attendant to shock, traumatic injury, sepsis, the administration of immunomodulators (such as tumor necrosis factor (TNF) for chemotherapy), as well as other situations. Thus, the risk of hypotension affects a significant number of persons throughout the world. For example, septic shock, a potentially lethal complication of bacterial infections, affects 150,000 to 300,000 patients annually in the United States alone.[1]

The cardiovascular collapse and multiple metabolic derangements associated with septic shock are due largely to bacterial endotoxin (ET), which has been shown to elicit a septic shock-like condition when administered to animals[2]. ET is known to stimulate the synthesis and release of several cytokines and biological mediators having hypotensive activity; among the factors released, TNF, platelet activating factor (PAF), prostacyclin and complement-derived C5a anaphylatoxin have been proposed as contributors to the cardiovascular collapse of septic shock[3-6].

Although it has been shown that animals pretreated with anti-TNF antibodies[7], PAF receptor antagonists[8], and prostacyclin synthesis inhibitors[9] may be protected against septic shock, the relative importance of these mediators in the pathology of septic shock is presently uncertain.

There is also evidence that some of these mediators may act indirectly via release of secondary mediators. Thus, the finding that anti-TNF antibodies have little or no protective effect when given after ET exposure[7] suggested to the present inventors that TNF stimulates the production of another factor that is the actual hypotensive agent. Once initiated, synthesis and release of that factor may continue even in the absence of detectable TNF. In 1980, Furchgott et al. (1980)[10] demonstrated that endothelial cells, which line blood vessels, can be stimulated to release a substance which relaxes vascular smooth muscle (i.e., causes vasodilatation). Since the chemical nature of this substance was completely unknown, it was simply named endothelium-derived relaxing factor (EDRF). It is hypothesized that many naturally-occurring substances which act as physiological vasodilators mediate all or part of their action by stimulating release of EDRF; these substances include, acetylcholine, histamine, bradykinin, leukotrienes, ADP, ATP, substance P, serotonin, thrombin and others.

The extremely short lifetime of EDRF (several seconds) hampered early efforts to chemically identify this molecule. In 1987, several laboratories suggested that EDRF may be nitric oxide (NO•), which spontaneously decomposes to nitrate and nitrite.[10,11] However, the fundamental problem in accepting this NO• hypothesis was that mammalian systems were not known to contain an enzymatic pathway which could synthesize NO•; additionally, a likely precursor for NO• biosynthesis was unknown.

After observing that the arginine analog L-N$\omega$-methylarginine (L-NMA) could inhibit vascular EDRF/NO• synthesis induced by acetylcholine and histamine, and that EDRF/NO• synthesis could be restored by adding excess L-arginine, certain of the present inventors proposed that arginine was the physiological precursor of EDRF/NO• biosynthesis[10]. Several of the present inventors later demonstrated that inhibition of EDRF/NO• synthesis in the anesthetized guinea pig resulted in an increase in blood pressure.

The present inventors have since been able to partially characterize the enzyme responsible for NO• synthesis. This enzyme has been designated nitric oxide synthase. Nitric oxide synthase is now known to oxidize a terminal nitrogen of the guanidino group of arginine, resulting in production of nitric oxide and citrulline. Macrophage-derived nitric oxide is now considered an important tumoricidal and bactericidal agent.

It has been reported that macrophages become "activated" by 12-36 hour after treatment with gamma-interferon, bacterial endotoxin and various cytokines in vitro. However, this in vitro "activation" system has been associated only with the initiation of tumor cell killing.[12] In addition, none of the literature or studies available prior to the present inventors work associated hypotension with nitric oxide. In addition, there currently does not exist definitive evidence of the involvement of macrophages with hypotension.

Macrophages are a quantitatively insignificant component of normal blood vessel walls, and have never been shown to play a role in blood pressure regulation; i.e., there existed no biochemical, physiological or immunological data to suggest that macrophages had any role in pathological hypotension. Thus, the inventors sought to investigate the role of nitric oxide in systems relevant to the manifestation of hypotension, specifically the role of cytokine-induced pathological hypotension, particularly on cells which comprise blood vessel walls.

In both clinical and animal studies on the effects of biological response modifiers, a major dose limiting toxicity has been hypotension and vascular leakage. The inventors have observed that endotoxin and tumor necrosis factor can induce over production of nitric oxide in animals.[23,24] Nitric oxide is a vasoactive substance which controls resting blood pressure.[13,14] This led the present inventors to postulate that hypotension in humans resulting from administration of biological response modifiers or from the development of overwhelming bacterial infections is due to excessive production of nitric oxide in sufficient concentration to cause excessive loss of systemic vascular resistance. However, macrophages are known to compose quantitatively only an insignificant component of normal blood vessel walls. Moreover, as a practical matter, it was unlikely that the amount of nitric oxide generated by circulating macrophages would be sufficient to elicit a "hypotensive" effect physiologically, as nitric oxide is not produced in vast enough quantities by the limited number of macrophages in blood vessel walls to produce such a pronounced physiological response. This, together with the recognized short half-life nitric oxide in vivo (3–5 seconds), opposed the theory that macrophage-derived nitric oxide was involved in hypotension.

The inventors postulated that: 1) other cell types were possibly linked to pathological hypotension, such as those cells associated with blood vessel walls (endothelial cells and vascular smooth muscle cells); 2) vascular (e.g., endothelial) cells may be stimulated to produce NO• by stimuli similar to those stimuli found to trigger NO• generation by macrophage; and 3) septic shock (i.e., systemic vasodilatation induced by bacterial endotoxin) may result from massive activation of NO• biosynthesis by cells which are a quantitatively significant component of normal blood vessel walls.

The inventors also observed that nitric oxide is derived from the amino acid L-arginine.[15] L-arginine is a typical ingredient in commercially available TPN (total parenteral nutrition) formulations.

As hypotension has been observed in patients maintained on standard TPN formulations, a potential valuable improvement in managing the risk of hypotension in these TPN-receiving patients is postulated by the inventors to be provided through a modified TPN formulation which reduces or eliminates the potential synthesis of nitric oxide. As the present inventors have observed that nitric oxide is derived from the amino acid arginine through the action of nitric oxide synthase, the modification of a TPN formulation to reduce or more preferably eliminate the availability of arginine (or the production of dietary arginine) will reduce the production of nitric oxide and the hypotensive effects nitric oxide causes in patients receiving or producing endotoxin, or receiving tumor necrosis factor, or any other of a variety of biological response modifiers. The effects of lowered arginine levels on blood pressure in a hypotensive animal are provided in the inventors prior application, U.S. Ser. No. 767,265, filed Sep. 27, 1991, the Specification of which is specifically incorporated herein by reference and specific reference to herein made.

Interleukin-1-α (IL-1) has been shown to enhance the restoration of peripheral blood leukocytes in mice myelosuppressed by cytotoxic chemotherapeutic agents.[16] In addition, IL-1 inhibits growth of murine tumors in vitro and in vivo and is cytocidal for several tumor cell lines.[17,18] Clinical trials in conjunction with the National Cancer Institute are currently underway to assess the efficacy of IL-1 as an immunorestorative agent in cancer patients exhibiting myelosuppression secondary to chemotherapy. In these trials, the does-limiting side effect of IL-1 is hypotension,[19-21] a complication that may prevent the administration of therapeutically effective doses of IL-1.

The association of IL-1 with compromised cardiovascular function is well documented in both animal and patient studies. thus, Dinarello et al.[22] have shown that administration of IL-1 causes a shock-like syndrome in rabbits, an effect they attributed to the overproduction of cyclooxygenase products. These authors also have shown a synergistic association between exogenous IL-1 and tumor necrosis factor (TNF) in causing shock. There is now considerable evidence that shock due to exposure to endotoxin (i.e., septic shock) is associated with increased endogenous production of both TNF and IL-1.[23] The critical role of IL-1 in endotoxic shock is substantiated by recent reports showing that administration of a human recombinant IL-1 receptor antagonist improves survival[24] and prevents the development of hypotension[25] in rabbits given endotoxin.

The inventors have previously shown that pathologic overproduction of nitric oxide (NO•)—initially characterized as endothelium-derived relaxing factor[10,11]—mediates the hypotension caused by the administration of TNF to dogs.[26] This data has also been described in the inventors patent application U.S. Ser. No. 406,909, filed Sep. 13, 1989, now U.S. Pat. No. 5,028,627, the Specification of which is specifically incorporated herein by reference. U.S. Ser. No. 838,814 filed Mar. 13, 1992 by the present inventors, is a continuation application of U.S. Pat. No. 5,028,627. The present disclosure is a continuation of U.S. Ser. No. 838,814. U.S. Ser. No. 838,814, is specifically referred to herein for purposes of establishing a continuous chain of copendency with the present application.

NO• is a short-lived but potent vasodilator formed enzymatically by oxidation of one of the two equivalent guanidino (i.e., omega) nitrogens of L-arginine in a reaction catalyzed by nitric oxide synthase.[27,28] Several $N^\omega$-substituted arginine analogues are effective inhibitors of nitric oxide synthase,[29-33] and some have been shown to inhibit NO• production in vivo.

Some of these $N^\omega$-substituted arginine analogs include $N^\omega$-methyl-L-arginine (NMA), NNA ($N^\omega$-nitro-L-arginine) and NAA ($N^\omega$-amino-L-arginine). Some enthusiasm has been generated in regard to the use of nitric oxide inhibitors, such as NMA, as antihypotensive agents. However, this prospect has been tempered by the recent demonstration that very large doses of NMA demonstrates an increase in mortality in endotoxic rodents,[34] while other studies have indicated that NMA increases hepatic damage following administration of endotoxin to rats.[35] The inventors own work has also shown that treatment with large doses of arginine analogs, such as NMA results in lower cardiac output in vivo while increasing blood pressure, the results of which could compromise oxygen delivery to critical organs. Therefore, methods and regimens which could optimize the potential normotensive action of these agents at lower doses would make these agents significantly more acceptable and useful in the clinical setting.

A method which would maximize the beneficial antihypotensive effects of low physiological arginine concentrations, for example, by the maintenance of an animal, on an arginine-free dietary support (TPN), coupled with moderate doses of a nitric oxide synthase inhibitor would provide a significant advantage in managing an animal with hypotension or at risk of developing hypotension.

SUMMARY OF THE INVENTION

The present disclosure presents a unique and potentially clinically useful therapeutic regimen proposed for the treatment of hypotension in an animal, including humans. In one embodiment of the invention, the therapeutic regimen comprises administering to a subject a therapeutically effective amount of an arginine-free parenteral formulation and administering a therapeutically effective amount of a nitric oxide synthase inhibiting arginine analog. The particular parenteral formulation of the regimen most preferably comprises a mixture of essential and nonessential amino acids, together in a pharmacologically acceptable excipient.

The arginine analogs of the present invention may be administered concurrently with or subsequent to the administration of the parenteral formulation. Most preferably, the parenteral formulation is administered, in an amount sufficient to reduce physiological concentrations of arginine prior to the administration of the arginine analog.

While any number of arginine analogs having an anti-hypotensive effect may be used in conjunction with the described therapeutic regimen, those arginine analogs most preferred include $N^\omega$-methyl-L-arginine, $N^\omega$-amino-L-arginine, $N^\omega$-nitro-L-arginine, or a mixture thereof. Most preferably, the arginine analog of choice for use in the described therapeutic regimen is $N^\omega$-methyl-L-arginine or $N^\omega$-amino-L-arginine. The therapeutically effective amount of these particular analogs may be defined as between about 0.1 mg/kg and about 100 mg/kg. In a more narrowly defined aspect of the invention, the therapeutically effective amount of $N^\omega$-methyl-L-arginine is a dose of between about 10 mg/kg and 30 mg/kg. The dose of arginine analog, such as $N^\omega$-methyl-L-arginine most preferred is about 20 mg/kg. These dose ranges may also be used for other arginine analogs with nitric oxide inhibiting activity in the practice of the present invention.

The arginine-free parenteral formulation of the described therapeutic regimen may be defined further as including a mixture of essential and nonessential amino acids. This mixture of essential and nonessential amino acids comprises: about 3–4 g/l isoleucine, about 4–6 g/l leucine, about 3–4 g/l lysine, about 1–2 g/l methionine, about 1–2 g/l phenylalanine, about 2–3 g/l threonine, about 0.5–1.5 g/l tryptophan, about 3–4 g/l valine, about 4–5 g/l alanine, about 1–2 g/l histidine, about 3–4 g/l proline, about 1–2 g/l serine, about 0.25–0.75 g/l tyrosine, about 4–5 g/l glycine and about 2–3 g/l aspartic acid. Again, the parenteral formulation of the therapeutic regimen is arginine-free. The pharmacologically acceptable excipient of the parenteral formulation is most preferably a Ringers solution or saline. Of these, saline is the most preferred excipient. Ornithine (about 1–2 g/l) and/or citrulline may be added to the formulation to enhance and maintain metabolic requirements of the urea cycle in the animal.

While the arginine analogs of the therapeutic regimen may be administered according to any administration route known to those of ordinary skill in the medical art, such as through oral, parenteral or enteral routes, the arginine analog is most preferably administered via a parenteral route, such as by an IV, IP or subcutaneous administration. Of these, intravenous administration of the arginine analog is most preferred, particularly through IV bolus treatment.

According to the described therapeutic regimen, the parenteral formulation is most preferably to be administered prior to the administration of the arginine analog. In addition, the parenteral formulation is to be administered in an amount sufficient to reduce plasma concentrations of arginine in the animal, most preferably to an amount less than normal physiological levels. For example, the amount of the parenteral formulation sufficient to reduce plasma concentrations of arginine in an animal may constitute a continuous intravenous feeding of the formulation described herein (arginine-free) for at least 2 hours prior to administration of the arginine analog. In a most preferred aspect of the regimen, the arginine analog is administered via an intravenous route to the animal after an initial parenteral feeding has been established. Alternatively, the arginine analog may be administered as a separate treatment concurrently with establishment of the animal on the above-described parenteral formulation.

In still another aspect of the invention, a method for treating hypotension in an animal is provided. In one embodiment, this method comprises identifying an animal having a systolic blood pressure of less than about 100 mm Hg, administering to said animal an anti-hypotensive parenteral formulation comprising an arginine-free mixture of essential and nonessential amino acids, administering currently with the formulation or subsequent to the formulation a therapeutically effective amount of an arginine analog capable of inhibiting nitric oxide, monitoring the blood pressure of said animal over a period of at least 24 hours, and maintaining the animal on the formulation and the arginine analog until a systolic blood pressure of at least about 100 mm Hg is detected. Detecting and monitoring blood pressure in an animal having a systolic blood pressure of less than 100 mm Hg may be achieved using standard blood pressure monitoring techniques, such as use of a blood pressure cuff for measurement of blood pressure in a human, for example, or though use of an indwelling arterial catheter connected to a pressure transducer (known to those of skill in the medical arts as an "arterial line").

The mixture of essential and nonessential amino acids is as described herein, and may also include ornithine or citrulline, or both. Ornithine and/or citrulline may be included to maintain metabolic requirements of the urea cycle.

The therapeutic regimens and methods of the present invention may be employed in the treatment of hypotension in various animal species. It is anticipated that the claimed therapeutic regimens and methods may most preferably be employed in the treatment of a human.

According to the described method, the arginine analog is most preferably $N^\omega$-methyl-L-arginine, $N^\omega$-amino-L-arginine, $N^\omega$-nitro-L-arginine or a mixture thereof. Most preferably, the arginine analog of choice to be used in conjunction with the described method is $N^\omega$-methyl-L-arginine. The anti-hypotensive parenteral formulation of the method most preferably comprises the following concentration of essential and nonessential amino acids: about 1–2 g/l ornithine, about 3–4 g/l isoleucine, about 4–6 g/l leucine, about 3–4 g/l lysine, about 1–2 g/l methionine, about 1–2 g/l phenylalanine, about 2–3 g/l threonine, about 0.5–1.5 g/l tryptophan, about 3–4 g/l valine, about 4–5 g/l alanine, about 1–2 g/l histidine, about 3–4 g/l proline, about 1–2 g/l serine, about 0.25–0.75 g/l tyrosine, about 4–5 g/l glycine and about 2–3 g/l aspartic acid, together in a pharmaceutically acceptable excipient. Again, ornithine (about 1–2 g/l) and/or citrulline may be added to the formulation for added nutritional value and to maintain proper physiological balance of urea cycle substrates.

Where the arginine analog of choice is $N^\omega$-amino-L-arginine, the therapeutically effective concentration of the analog may preferably constitute a dose of between about 0.1 mg/kg to about 100 mg/kg. An even more preferred concentration range of the arginine analog, $N^\omega$-amino-L-arginine, is between about 10 mg/kg to about 30 mg/kg. Even more preferably, the therapeutically effective concentration of the arginine analog $N^\omega$-amino-L-arginine is about 20 mg/kg. Accordingly to a most preferred embodiment of the described method, the arginine analog is to be administered intravenously, such as in a single bolus dose.

In still another aspect of the claimed invention, a method for treating chemotherapeutic agent-related hypotension in an animal receiving a chemotherapeutic agent is provided. This method in one embodiment comprises monitoring an animal receiving a chemotherapeutic agent for a decrease in systolic blood pressure to less than 100 mm Hg to detect an animal with systemic hypotension, treating the animal with a therapeutic regimen comprising an arginine-free parenteral formulation concurrently with or followed by the administration of a therapeutically effective concentration of an arginine analog capable of inhibiting nitric oxide synthase, and maintaining the animal on the therapeutic regimen until an increase of systolic blood pressure to at least about 100 mm Hg is detectable.

Detecting and monitoring blood pressure in an animal may be accomplished using those techniques well known to those of skill in the medical arts, such as via a blood pressure cuff or arterial line as described herein.

It is contemplated that the aforedescribed method may be used in the treatment of a human receiving a chemotherapeutic agent. By way of example, chemotherapeutic agents associated with at least a risk of the development of systemic hypotension include tumor necrosis factor, interleukin-2 and interleukin-1 alone or in combination with interferons or each other.

In a most preferred aspect of the aforedescribed method, the arginine-free parenteral formulation comprises the mixture of essential and non-essential amino acids already described herein together in a pharmacologically acceptable excipient. It is contemplated that the therapeutically effective concentration of the arginine analog capable of inhibiting nitric oxide production to be used in conjunction with the method is between about 0.1 mg/kg and about 100 mg/kg. A most preferred and narrowly defined range of arginine analog to be used in the described method is between about 10 mg/kg and about 30 mg/kg. Most preferably, the therapeutically effective concentration of the arginine analog constitutes a dose of about 20 mg/kg.

Those arginine analogs most preferred in conjunction with the aforedescribed method include $N^\omega$-methyl-L-arginine, $N^\omega$-amino-L-arginine, or $N^\omega$-nitro-L-arginine, or a mixture thereof. Among these, $N^\omega$-methyl-L-arginine is most particularly preferred.

In still another aspect of the invention, a method for treating hypotension attendant septic shock is provided. In one embodiment of the method, a therapeutically effective amount of an arginine-free parenteral formulation as described herein is administered to an animal concurrently with or prior to the administration of a therapeutically effective amount of an arginine analog capable of inhibiting nitric oxide synthase, and maintaining the animal on the arginine-free parenteral formulation until a systolic blood pressure of at least about 100 mm Hg is detectable in the animal. By way of example, hypotension attendant septic shock is noted in animals with bacterial endotoxin-related septic shock. While any of a variety of animals may be treated for hypotension attendant septic shock according to the aforedescribed method, it is contemplated that the method may find particular applicability in the treatment of humans suffering from such a condition. In particularly preferred embodiments of the described method, the arginine analog preferred is $N^\omega$-methyl-L-arginine, $N^\omega$-amino-L-arginine, $N^\omega$-nitro-L-arginine or a mixture thereof. Of these arginine analogs, $N^\omega$-methyl-L-arginine or $N^\omega$-amino-L-arginine is most preferred.

According to one embodiment of the method, the therapeutically effective concentration of the arginine analog is a dose of between about 10 mg/kg and about 30 mg/kg body weight of the animal. Even more preferably, the therapeutically effective amount of the arginine analog is a dose of about 20 mg/kg body weight of the animal.

In still another aspect of the invention, a method for providing nutritional support for an animal with hypotension or at risk of developing hypotension is provided. This method comprises administering to the animal a nutritionally supportive arginine-free parenteral formulation concurrently with or prior to treatment with a hypotension inhibiting concentration of a nitric oxide synthase inhibitor. Subjects at risk of developing hypotension include subjects in shock or having had experienced some sort of trauma, subjects exposed to endotoxic agents or a chemotherapeutic agent having hypotensive activity.

By way of example, the nitric oxide synthase inhibitors of the present invention include $N^\omega$-methyl-L-arginine, $N^\omega$-amino-L-arginine or $N^\omega$-nitro-L-arginine, or a mixture thereof. In a most preferred aspect of the described method, the nitric oxide inhibitor of choice is $N^\omega$-methyl-L-arginine. The essentially arginine-free parenteral formulation comprises a mixture of essential and non-essential amino acids as described herein and may be supplemented with ornithine, citrulline, or both, to ensure metabolic requirements of the urea cycle in the animal.

The nitric oxide inhibitors of the present invention may be even more specifically described as a nitric oxide synthase inhibitors.

In a more particularly defined embodiment of the aforedescribed method, the hypotensive inhibiting concentration of the nitric oxide synthase inhibitor is between about 0.1 mg/kg and about 100 mg/kg. Even more preferably, the range of concentration of the nitric oxide synthase inhibitor contemplated as effective in the aforedescribed method is between about 10 mg/kg and about 30 mg/kg. In a most particularly preferred embodiment of the method, the hypotensive inhibiting concentration of the nitric oxide synthase inhibitor is a dose of about 20 mg/kg, particularly where the nitric oxide synthase inhibitor is $N^\omega$-methyl-L-arginine. It is also contemplated by the present inventors that the described method for providing nutritional support for an animal with hypotension or at risk of developing hypotension will be beneficial in the treatment of humans.

A TPN regimen of low or essentially arginine-free formulations is proposed in conjunction with a treatment regimen of nitric oxide synthase inhibitors to reduce, if not eliminate, the risk of hypotension and septic shock in patients with bacterial infections. Clinical regimens which typically require the administration of a TPN formulation include, for example, nutritional support of cancer patients and others who have no or limited ability to tolerate oral feeding.

Preferred $N^\omega$-substituted arginine analogs of the L configuration for uses as described herein include $N^\omega$- aminoarginine, $N^\omega$-nitroarginine, and $N^\omega$-alkyl arginines such as $N^\omega$-methylarginine, $N^\omega$-ethylarginine, $N^\omega$-propylarginine or butylarginine. Therapeutically effective amounts of the substituted or disubstituted arginine analogs inhibit production in the animal or patient of nitric oxide from arginine, thus obviating its hypotensive effects.

Notwithstanding the accumulated evidence supporting synthesis of NO•, it is understood by those skilled in the art that other nitrogen oxides may be present and may be active in reducing blood pressure.

The present invention also contemplates the use of additional guanidino-based inhibitors of nitric oxide synthesis for the treatment of hypotension, septic shock, and related conditions, in combination with the arginine-free parenteral formulations of the present invention. These guanidino-based inhibitors comprise molecules that are smaller than L-arginine (molecules containing 5 or fewer carbon atoms). The inventors have found that guanidino containing amino acids that include a carbon chain of one less carbon than arginine do not function as nitric oxide synthase inhibitors, while guanidino containing amino acids that have a carbon chain length one carbon longer than arginine have some albeit reduced, nitric oxide synthase inhibiting activity. Guanidino containing amino acids which include a carbon chain two carbons longer than L-arginine were found not to have nitric oxide inhibiting activity. The present inventors have also found that arginine analogs that may inhibit nitric oxide synthesis (or nitric oxide synthase) do not require a carboxyl group or one of the amino groups of the native arginine molecule to retain nitric oxide synthase inhibiting activity. Therefore, the present invention is intended to encompass nitric oxide synthase inhibitors and arginine analogs that include these guanidino-based compounds. Examples of these guanidino-based compounds include amino guanidine and $N^G$-alkyl-$N^{G'}$-amino guanidines where the alkyl group contains 1 to 3 carbons.

Abbreviations used in the drawings and other places in this application include the following.

ACh=acetylcholine
BAEC=bovine aortic endothelial cells
B.P.=blood pressure
CO=Cardiac output
EDRF=Endothelium-Derived Relaxing Factor
ET=endotoxin
GP=guinea pig
HIST=histamine
IFN=gamma-interferon
IV=Intravenous
L-Arg=L-arginine
LPS=lipopolysaccharide (endotoxin)
MAP=mean arterial pressure
MBEC=murine brain endothelial cells
NE=norepinephrine
NO•=Nitric Oxide
NAA=$N^\omega$-L-amino-L-arginine
L-NMA=L-NMMA=$N^\omega$-methyl-L-arginine
NNA=$N^\omega$ nitro L-arginine
PAF=Platelet Activating Factor
PPS=Platelet—poor, plasma-derived serum
SAP=Systemic arterial pressure
SNP=sodium nitroprusside
SVR=Systemic vascular resistance
TNF=Tumor Necrosis Factor
TPN=Total Parenteral Nutrition Formulation

BRIEF DESCRIPTION OF THE DRAWINGS

FIG. 2A: Comparison of nitrite synthesis inhibition in smooth muscle cells by the L-isomers of NAA, NMA, and NNA and by the D-isomer of NMA. FIG. 2B: Concentration dependence of nitrite synthesis inhibition in smooth muscle cells by NAA as a function of different L-arginine concentration in the culture medium. Confluent monolayers of smooth muscle cells in 96-well microtiter plates were treated with a combination of 100 ng/ml IL-1 and 50 ng/ml IFN-γ for 24 hours. Cells were then washed with Hanks' balanced salt solution, and fresh medium containing the indicated concentration of L-arginine was added. Points indicate means±SD of nitrite production, expressed as percent of control, during a 16-hour exposure to arginine analogues (n=3–4). FIG. 2C: Effect of NAA on smooth muscle cell NO• synthase. Cytosol from cytokine-induced smooth muscle cells (~2 µg protein) was incubated with 1 mM L-arginine, 0.5 mM NADPH, 1 mM dithiothreitol, 10 µM flavinadenine dinucleotide, 10 µM tetrahydrobiopterin, and 0.1 U/ml dihydropteridine reductase in a total volume of 100 µL. The time course of $Fe^{2+}$-myoglobin oxidation was measured in the absence (control) or presence of 300 µM NAA (+NAA). The inventors have also observed that myoglobin oxidation showed an absolute dependence on L-arginine and NADPH. Points indicate the time course of change in rate of NO• synthesis in a representative experiment which was repeated three times.

DETAILED DESCRIPTION OF THE PREFERRED EMBODIMENTS

Figure 1:
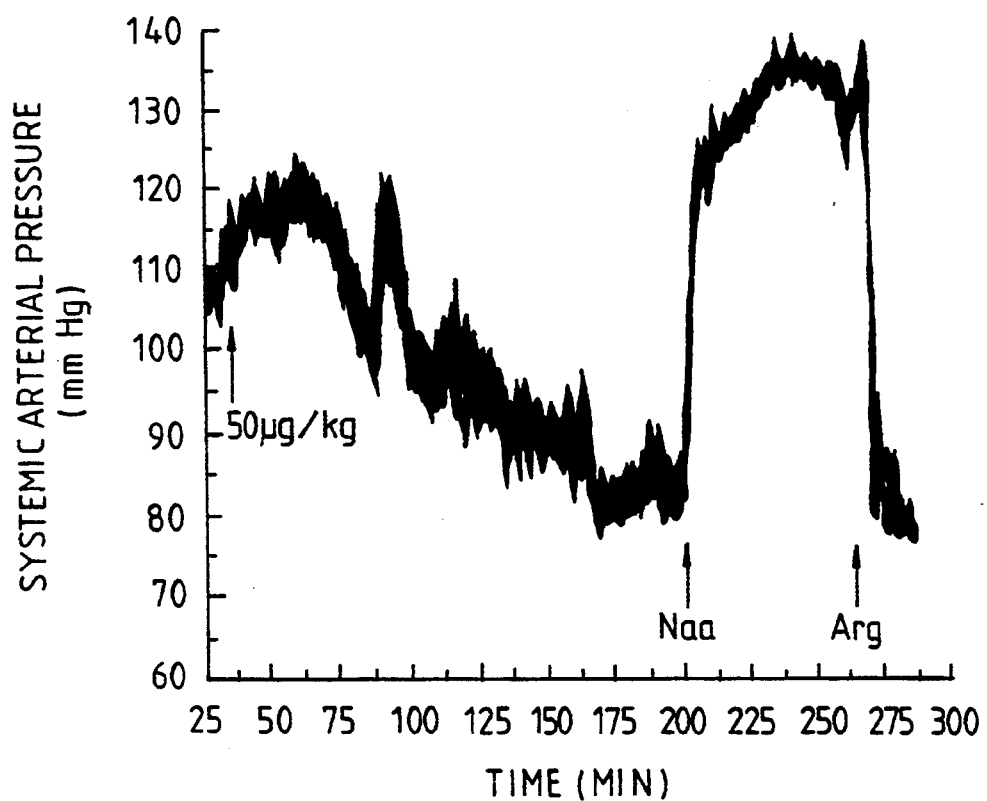
FIG. 1—Reversal of hypotension associated with the administration of IL-1 to dogs. The tracing shown is a representative experiment that was repeated four times. Each dog was anesthetized and incubated as described herein, and baseline cardiovascular data were monitored for 30 minutes. IL-1 was dissolved in phosphate-buffered saline (pH 7.4) containing 1 mg/ml of dog albumin, and the resulting solution was infused intravenously for three minutes to deliver a dose of 50 µg/kg. MAP was continuously monitored; when a stable nadir was reached and maintained for more than 10 minutes or when MAP dropped below 50 mm Hg, NAA (20 mg/kg in 10 ml phosphate-buffered saline) was administered by intravenous infusion for 30 seconds. Sixty minutes after MAP was restored to baseline or higher values, L-arginine (400 mg/kg in 20 ml phosphate-buffered saline) was administered by slow intravenous infusion for 5 minutes. Anesthetized dogs given IL-1 (50 µg/kg) developed a progressive, moderately severe hypotension, with MAP decreasing from a baseline of 111+/−7 mm Hg to 80+/−2 mm Hg within about 3 hours. Hypotension was rapidly reversed by the intravenous administration of a single bolus dose of NAA (20 mg/kg, 88 umol/kg), with MAP increasing by from 46+/−9 mm Hg (58% to 125+/−8 mm Hg.
Figure 2A:
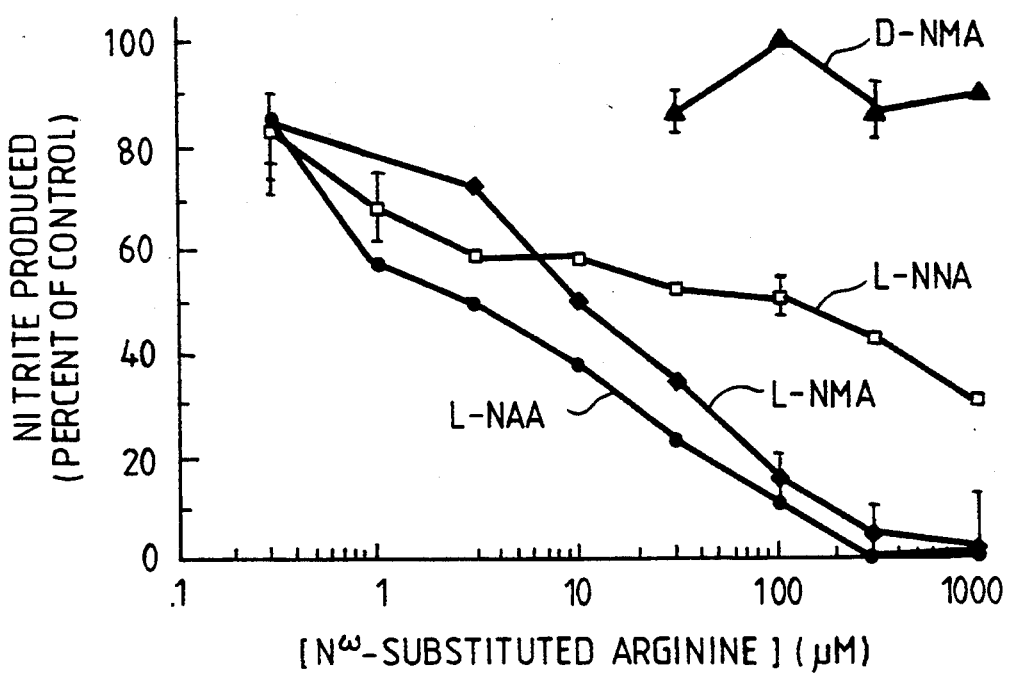
FIGS. 2A–2C—Inhibition of IL-1-activated NO• production by $N^\omega$-substituted arginine analogues.
Figure 2B:
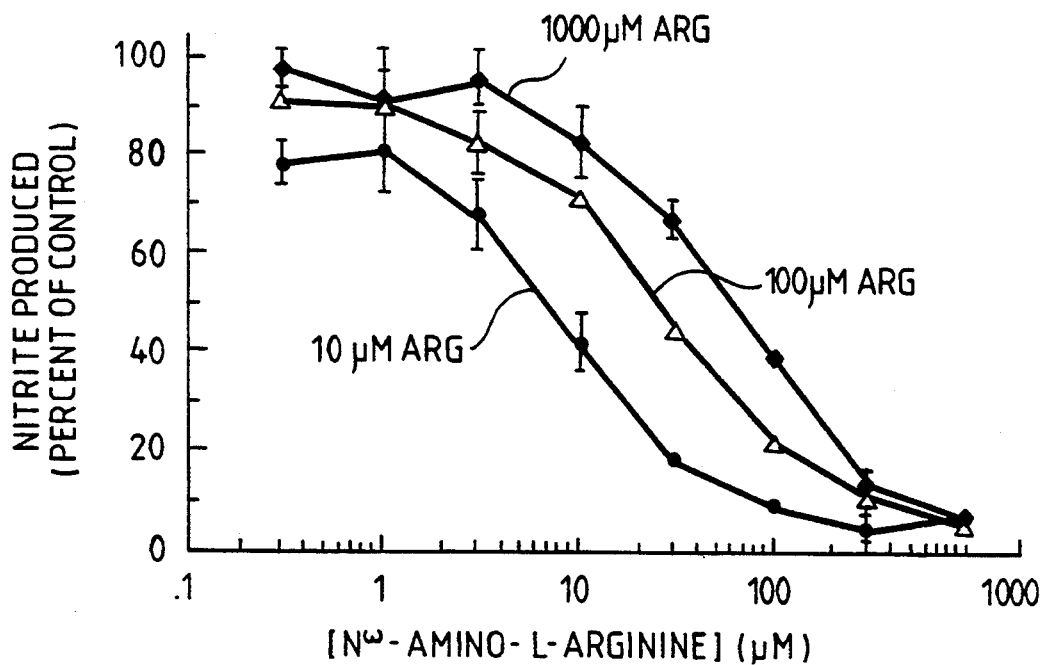
Figure 2C:
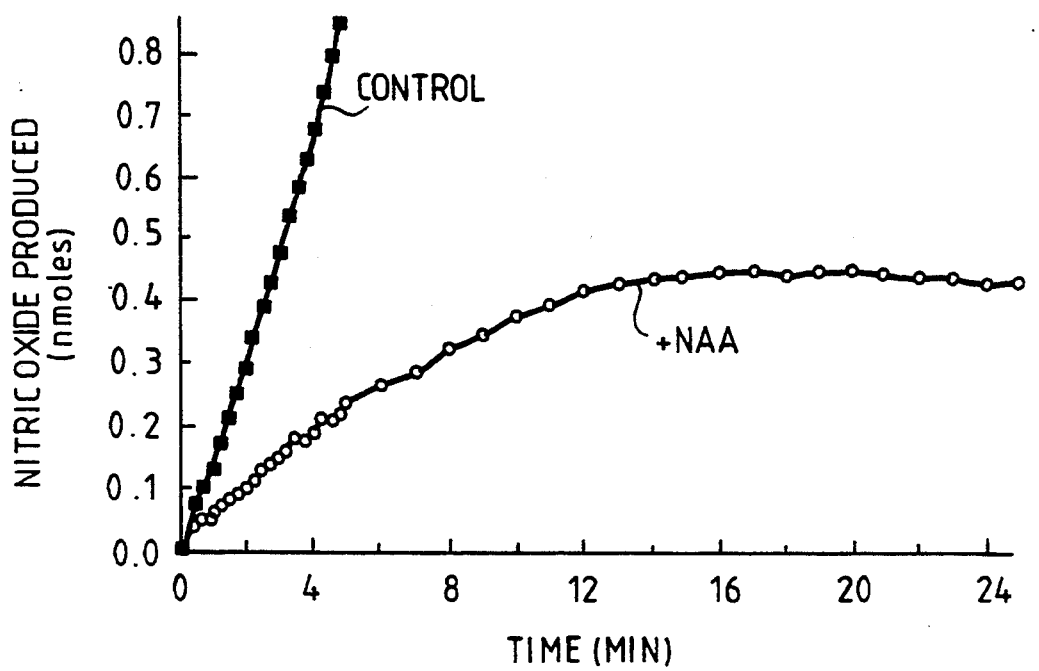

The present invention provides for unique therapeutically useful regimens for treating hypotension, such as that attendant septic shock or treatment with certain chemotherapeutic agents such as TNF, IL-1 or IL-2. The various regimens and formulations thereof described in conjunction with the present invention include the administration of an arginine-free parenteral formulation. The formulation is to be administered either concurrently with or followed by the treatment of the animal with an arginine analog capable of inhibiting nitric oxide, production. Agents which are capable of inhibiting nitric oxide production include, arginine analogs capable of inhibiting nitric oxide synthase, and include NMA, NAA, NNA, or a mixture thereof.

Human recombinant IL-1-$\alpha$ (hereafter referred to as IL-1; specific activity, $2 \times 10^7$ lymphocyte-activating factor units/mg) was produced by Dainippon Pharmaceutical Co. LTD. and provided by the National Cancer Institute. Human recombinant IL-1 receptor antagonist was produced by Synergen, Co. and was provided by Drs. Lyle Moldawer and Stephen Lowry, Department of Surgery, Cornell University Medical College. Rat interferon-$\gamma$ (IFN-$\gamma$) was obtained from Amgen Biologicals (Thousand Oaks, Calif.).

N$^\omega$-methyl-L-arginine (NMA) and NAA, hydrochloride salt, were synthesized as reported previously by Gross et al. (1990) (Biochem. Biophys. Res. Commun., 170:96–103) and Corbin (1974) (Anal. Biochem., 57:310–312), which references are specifically incorporated herein by reference for this purpose. Except where indicated, all biochemical reagents were obtained from Sigma Chemical Co. (St. Louis, Mo.). Cell culture media and reagents, unless otherwise noted, were from Whittaker Bioproducts (Walkersville, Md.).

Cell Culture

Mouse A375 melanoma cells were provided by Dr. E. Kleinerman, The University of Texas M.D. Anderson Cancer Center. Cells were maintained in Dulbecco's modified Eagle medium and Ham's F-12 medium (1:1) containing 10 mM HEPES buffer (pH 7.4) and 10% fetal bovine serum. All tissue culture reagents contained less than 0.25 ng/ml endotoxin as measured by the limulus amebocyte assay. Murine D10 T cells were obtained from the American Type Culture Collection (Rockville, Md.).

Aortic smooth muscle cells were cultured by explanting segments of the medial layer of aortas from adult male Fischer 344 rats. Aortas were removed aseptically and freed of adventitial and endothelial cells by scraping both the luminal and abluminal surfaces. Medial fragments were allowed to attach to Primaria 25-cm$^2$ tissue culture flasks (Becton-Dickinson, Lincoln Park, N.J.) which were kept moist with growth medium until cells emerged. Cultures were fed twice weekly with medium 199 containing 10% fetal bovine serum, 25 mM HEPES buffer (pH 7.4), 2 mM L-glutamine, 40 $\mu$g/ml endothelial cell growth supplement (Biomedical Technologies, Inc. (Stoughton, Mass.), and 10 $\mu$g/ml gentamicin (GIBCO). When primary cultures became confluent, they were passaged by trypsinization, and explants were discarded. For these studies, cells from passages 12–14 were seeded at 20,000/well in 96-well plates and were used at confluence (60,000–80,000 cells/well). The cells exhibited the classic SMC phenotype with hill and valley morphology and stained positively for smooth-muscle actin.

Cell Respiration Assay

Rat aortic smooth muscle cells in 96-well microtiter plates were incubated for 90 minutes in RPMI-1640 medium containing 0.2 mg/ml 3-(4,5-dimethylthiazol-2-yl)-2,5-diphenyltetrazolium bromide (MTT), washed with Hands' balanced salt solution, and solubilized in 100 $\mu$l of dimethyl sulfoxide. The extent of reduction of MTT to formazan within cells, quantitated by measurement of the optical density at 550 nm (OD$_{550}$), was taken as an indicator of cellular respiration. The assay is more thoroughly described by Klostergaard et al. (1987) (J. Immunol. Methods, 101:97–108), which reference is specifically incorporated herein by reference for this purpose.

IL-1-Induced Cell Proliferation Assay

Murine D10 cells, an IL-1-dependent T-cell line, were used to measure IL-1 mitogenic activity. Cell proliferation in the presence of IL-1 was assessed by incorporation of [$^3$H] thymidine as previously described by Bakouche et al. (1987) (J. Immunol., 138: 4249–4255), which reference is specifically incorporated herein by reference for this purpose.

IL-1-Induced Cytotoxicity Assay

IL-1-induced cytotoxicity was studied using A375 tumor cells plated at a density of 6000 cells per well in 96-well microtiter plates. After overnight attachment, IL-1 (3–300 ng/ml) was added in the presence or absence of NAA or NMA. After cells were incubated for 3 days, [$^3$H] thymidine was added (1 $\mu$Ci per well) for an additional 2 hours. Cells were harvested onto glass fiber disks (PHD Cell Harvester; Cambridge Technology, Inc., Watertown, Mass.). Disks were air dried overnight, and radioactivity was determined with a Model 1900TR Scintillation Counter (Packard Instrument Division, Downers Grove, Ill.).

Induction and Assay of Nitrite Synthesis in Smooth Muscle Cells

Rat aortic smooth muscle cells were incubated with RPMI-1640 medium containing 10% bovine calf serum, 25 mM HEPES buffer (pH 7.4), 2 mM glutamine, 80 U/ml: fungizone, and IL-1, IFN-$\gamma$, and various inhibitors at the concentrations indicated in the figure legends. At the desired times, nitrite concentration in the culture medium was measured using the standard Griess assay adapted to a 96-well microtiter plate reader.[36] The Griess assay is also described in Gross et al.[37] (1991), which reference is specifically incorporated herein by reference for this purpose. Thus, 100 $\mu$L of Griess reagent (0.5% sulfanilic acid, 0.05% naphthalenediamine, and 2.5% phosphoric acid) was added to an equal volume of culture medium, and the $OD_{550}$ was measured and related to nitrite concentration by reference to a standard curve. The background $OD_{550}$ of medium incubated in the absence of cells was subtracted from experimental values.

Preparation and Assay of Smooth Musole Cell NO• Synthase

Rat aortic smooth muscle cells were incubated with RPMI-1640 medium containing 10% bovine calf serum, 25 mM HEPES buffer 7.4), 2 mM glutamine, 80 µg/ml penicillin, 80 µg/ml streptomycin, 2 µg/ml fungizone, 30 µg/ml lipopolysaccharide (*Escherichia coli* 0111:B4), and 50 U/ml IFN-γ. Cells were harvested after 24 hours, and cytosol was prepared as described in the above cited Gross et al. (1991)[41] article. Cytosolic NO• synthase activity was assayed by the $Fe^{2+}$-myoglobin method described previously.

Studies of IL-1-Induced Hypotension in Dogs

Experiments were conducted on healthy mongrel dogs that were free of microfilaria and weighed 25–28 kg each. All protocols were approved by The University of Texas Animal Welfare Committee, and animal care met all standards prescribed in the "Guide for the Care and Use of Laboratory Animals" (Department of Health, Education and Welfare, Guide for the Care and "Use of Laboratory Animals Pub. No. 78-23, Washington, D.C., Health Department (1978). After an overnight fast, the dogs were anesthetized with pentobarbital (25 mg/kg given intravenously), orotracheally incubated, and ventilated with an animal respirator (Harvard Apparatus, South Natick, Mass.), using room air at a tidal volume of 15 ml/kg delivered at 14 breaths per minute and adjusted to normal pH and $CO_2$ tension. A catheter was placed percutaneously in the femoral artery, and a flow-directed thermodilution catheter was inserted through the jugular vein and positioned with the distal port in the pulmonary artery. Mean systemic arterial pressure (MAP), heart rate, cardiac output, and systemic vascular resistance were measured as previously described in Kilbourn et al. (1990) (*Biochem. Biophys. Res. Commun.*, 172:1132–1138), which reference is specifically incorporated herein by reference.

For purposes of the present invention, the term "cytostatic" is defined as that physiological state of a cell characterized by a lack of active cell division. Thus, a culture or group of cells which are in a "cytostatic" state are not actively dividing or which are growth inhibited (i.e., virtually no cell growth).

The terms "anti-hypotensive" and "non-hypotensive" are used interchangeably in defining the present invention. These terms are intended to denote the nature of the formulation as limiting the onset of hypotension through inhibition of nitric oxide synthase through decreased arginine concentrations and thus availability of serum arginine.

For purposes of the present invention, a "pressor" agent is defined as a pharmacological agent which causes an increase in blood pressure when administered to an animal. By way of example, phenylephrine is a "pressor" agent. However, other pressor agents would be expected to provide similar effects in the systems described herein. Other examples of pressor agents include dopamine, epinephrine, norepinephrine and phenylephrine.

Even though the present invention has been described with a certain degree of particularity, it is evident that many alternatives, modifications, and variations will be apparent to those skilled in the art in light of the following disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof unless specifically indicated to do so.

EXAMPLE 1

CORRELATION BETWEEN SERUM ARGININE LEVELS AND BLOOD PRESSURE IN VIVO

The present example is provided to demonstrate the correlation between plasma arginine levels and blood pressure. More specifically, the present example demonstrates a correlation between low plasma arginine levels and increased blood pressure in endotoxin-treated hypotensive animals.

The present example also demonstrates the utility for employing a parenteral formulation which is essentially arginine free or low enough in arginine to lower plasma arginine levels, to prevent or alleviate synthesis of nitric oxide, which in turn is shown to result in an increase in blood pressure. Maintenance of an animal on an arginine-free parenteral formulation and a nitric oxide synthase inhibitor, such as the arginine analogs NMA, NAA or NNA or a combination thereof, would therefore, according to the present invention, provide a method for even further augmenting the anti-hypotensive effect of both components of such a regimen, using significantly lower doses of arginine analogs than would otherwise be required in animals with normal or high physiological concentrations of arginine. The hypertensive effect of NAA and other nitric oxide inhibitors in vivo alone is also described in the present disclosure. The onset of life-threatening levels of low blood pressure, such as that typically attendant to cytokine-induced hypotension and septic shock would thus be prevented or alleviated in an animal.

The enzyme arginase was used to reduce plasma arginine levels in Sprague-Dawly rats (Weight per rat=250–300 gm). Arginase is an enzyme that converts L-arginine to L-ornithine+urea. The rats were anesthetized with ethyl ether and then pithed as described Shiply and Tilden ((1947), Proc. Soc. Exp. Biol. Med., 65:453–455). The animals were pithed prior to use in the present study so as to eliminate any neurological control of blood pressure.

Arginase was dissolved in sterile saline (1000 I.U./ml) and was administered by intravenous infusion at a rate of 300 I.U./min. for 20 min. One I.U. is the amount of arginase that converts 1 µmol of arginine to products per minute. Blood pressure was determined using a pressure transducer connected to an indwelling catheter placed in the carotid artery as described (Aisaka et al. (1989) BBRC, 160:881–886).

Serum arginine concentrations

The administration of arginase to pithed rats with or without exposure to endotoxin (15 mg/kg dose, ip), according to the dose outlined above, resulted in a decrease in plasma arginine levels of from 150 µM to ≦4 µM within a few minutes. Plasma arginine remained at levels ≦4 μM for at least 1 hour after the arginase infusion was stopped.

Blood pressure recording in the pithed rat

To record blood pressure, a tracheotomy was first performed on each rat, after which the rats were artificially respired with room air. The left common carotid artery was then cannulated in each rat for blood pressure measurement via a Statham pressure transducer (Hato Rey, Puerto Rico) and displayed on a physiogram (Grass Instruments, Quincy, Mass.). Heart rate was measured from the lead III electrocardiogram.

Two separate groups of animals were examined. The first group of animals, designated the "control" group, received no endotoxin. The blood pressure of the "control" group animals was measured at two different times, once before the administration of arginase and once after the administration of arginase.

The second group of animals, designated the endotoxin group, received a single dose of endotoxin of 15 mg/kg body weight, which was administered at least 6 hours prior to any subsequent arginase treatment. The blood pressure of all animals in both treatment groups was then measured at two different times, again once before arginase treatment and once after arginase treatment.

The results from this example are presented in Table 1.

TABLE 1

EFFECT OF REDUCED PLASMA ARGININE ON BLOOD PRESSURE

| Control Rats | No Arginase B.P. (mm Hg) | Average B.P. | Arginase B.P. (mm Hg) | Average |
|---|---|---|---|---|
| 1 | 61 | 59.8 ± 1.3 | 61 | 63.25 |
| 2 | 60 | | 60 | |
| 3 | 60 | | 64 | |
| 4 | 58 | | 68 | |

| Endotoxic Rats (15 mg/Kg) | No Arginase B.P. (mm Hg) | Average B.P. | Arginase B.P. (mm Hg) | Average |
|---|---|---|---|---|
| 1 | 36 | 33.2 ± 3.3 | 44 | 38.4 |
| 2 | 34 | | 40 | |
| 3 | 28 | | 28 | |
| 4 | 32 | | 36 | |
| 5 | 36 | | 44 | |

Blood pressure readings for 4 control pithed rats were 61, 60, 60, and 58 mm Hg (average 59.8±1.3 mm Hg) (See Table 1). Following administration of arginase, blood pressure was unchanged in two rats and increased by 4 and 10 mm Hg in 2 other rats (average increase 3.5±4.7 mm Hg, not statistically significant).

Blood pressure readings for 5 rats at 6 hours after giving 15 mg/kg lipopolysaccharide (endotoxin) by intravenous injection was 36, 34, 28, 32, and 36 mm Hg (average 33.2±3.3 mm Hg, See Table 1). Note that the endotoxin-treated rats were clearly hypotensive relative to the controls.

Following administration of arginase, blood pressure in the endotoxin-treated rats increased by 8, 6, 0, 4, and 8 mm Hg (average increase 5.2±3.3 mm Hg). The average blood pressure increase following arginase treatment of the endotoxic, pithed rats was 15.7% (statistically significant, $p<0.05$).

Overall, this study shows that reducing plasma arginine levels has no significant effect on blood pressure in control animals, but did have a significant effect on blood pressure readings in endotoxic animals. The lack of a demonstrated effect in control animals may be due to the slow rate of NO• formation in control animals, so as to negate any requirement for exogenous (i.e. plasma) arginine. Thus, a reduction in plasma arginine levels in such animals would not be a limiting factor for generating NO•.

In contrast, the rate of NO• formation in endotoxic animals is much faster than in control (non-endotoxic animals), and results in the development of hypotension. In these endotoxic animals, the cells making NO• must obtain extra arginine from the plasma. When plasma arginine is very low in endotoxic animals (i.e. after arginase administration), there is not enough arginine available to sustain a pathologically high rate of synthesis by cells associated with blood vessel walls (i.e., endothelial cells). Thus, the concentration of NO• is reduced, resulting in a concomitant reduction in the level of blood pressure reduction in the vasculature of the animal. Thus, depletion of serum arginine levels could be used to effect an increase in blood pressure in hypotensive animals.

Use of arginine-free TPN solutions, or solutions sufficiently low in arginine concentration so as to effect a sufficient reduction in plasma arginine levels adequate to limit nitric oxide synthesis, for example, to about 4 μM arginine or less (i.e., 4 nM arginine/ml serum arginine), are expected to have a beneficial effect comparable to that of arginase administration for preventing or treating hypotension, particularly hypotension in animals in septic shock.

EXAMPLE 2

CORRELATION BETWEEN ARGININE LEVELS AND RESPONSE TO PRESSOR AGENTS IN VIVO

The present example is provided to demonstrate the correlation between low plasma arginine levels and increased response to "pressor" agents in vivo in endotoxin-treated animals.

As a result of receiving endotoxin, the animals employed in the present study become hypotensive (low blood pressure). The present example therefore demonstrates the utility of the present combination therapeutic regimen in treating animals with hypotension, as the agents found by the present inventors to function as "pressor" agents, namely the arginine analogs NMA, NAA and NNA, are shown to have significant blood pressure increasing capabilities in animals which have lowered circulating arginine levels. Animals with physiologically "normal" blood pressure levels (at least 100 mm Hg) do not respond to the administration of pressor agents with the same degree of increase in blood pressure as the hypotensive animals with lowered circulating arginine levels.

Lower concentration doses of the pressor agents may thus be used to treat hypotensive animals to elicit an increase in blood pressure, therefore, simply by reducing the circulating arginine concentrations in the animal. This reduction in circulating arginine concentrations, most preferably, is accomplished through eliminating the dietary sources of arginine to the animal, such as by maintaining the animal on an arginine-free TPN solution, or through treating the animal with an arginine-lowering drug, such as arginase. In a most preferred embodiment, arginine levels in an animal are reduced by maintaining the animal on an arginine-free-parenteral solution.

The particular "pressor" agent employed in this example is phenylephrine. However, virtually any "pressor" agent could be employed with equal utility to demonstrate the physiological effects disclosed by the present inventors. It has previously been observed that in septic shock, patients are hypotensive and no longer respond well to the usual pressor drugs such as phenylephrine, dopamine and pinephrine. To determine if lowering plasma arginine would improve responsiveness, the present study was carried out in pithed rats. The lowering of plasma arginine concentrations in vivo through the administration of arginase is a technique employed in the present study to demonstrate the effects of pressor agents in an animal which was maintained on an arginine-free parenteral formulation (TPN) to provide a lowered plasma arginine concentration. As will be demonstrated, the hypertensive effect of a pressor agent is greatly enhanced in a hypotensive animal with lower plasma arginine.

Animals were pitbed as described in Example 1. Blood pressure measurements were obtained also as described in Example 1. Arginase was also prepared according to the method described in Example 1.

Both left and right jugular veins were cannulated for drug administration; and left jugular was used for bolus administration of phenylephrine and the right jugular vein was used for continuous infusion of arginase. All animals from both groups (Control and Endotoxin) received phenylephrine in sequential doses of 0.3, 1.0, 2.0, or 6.0 ug/kg.

The results from this example are presented in Table 2.

32 and 9 before arginase, respectively, and 9, 20 and 10 after arginase, respectively.

The data presented in Table 2 demonstrates that reducing plasma arginine levels through arginase treatment, enhances the "pressor" agent (such as phenylephrine) response in endotoxic animals, reducing the difference observed between endotoxic and control animal blood pressure increases at the same pressor agent dose. Moreover, endotoxic animals pretreated with arginase demonstrated an enhanced "pressor" effect (a statistically greater increase in blood pressure), compared to the pressor response observed in endotoxic animals receiving no arginase (See Table 2).

Endotoxin decreases an animals ability to present the normal hypertensive response (i.e., increase in blood pressure) to phenylephrine. Thus, compare the "Without Arginase" data of control and endotoxic rats at each dose of phenylephrine (Table 2). This effect occurs because the endotoxic animals are making large amounts of nitric oxide from arginine, and that causes hypotension and blunting of the response to phenylephrine.

Arginase administration improves the hypertensive response to a pressor agent, such as phenylephrine. Smaller differences were observed between control and endotoxic animals given arginase (indicating only a small loss of responsiveness) relative to the larger differences between control and endotoxic animals not given arginase (indicating a large loss in responsiveness).

For example, at a phenylephrine dose of 6 $\mu$g/kg, in animals not given arginase (i.e., having a higher serum arginine concentration), the pressor response to phenyl-

TABLE 2
EFFECT OF ARGINASE AND ENDOTOXIN ON BLOOD PRESSURE RESPONSE TO A PRESSOR AGENT

| Phenylephrine dose S.D. | Blood Pressure Increase (mm Hg) | | | |
|---|---|---|---|---|
| | Without Arginase | | With Arginase | |
| | Raw Data | Ave. ± S.D. | Raw Data | Ave.± |
| Study #1: Control Animals | | | | |
| 0.3 $\mu$g/kg | +16,14,32,9 | 17.8 ± 5.0 | +4,9,20,10 | 13.3 ± 2.5 |
| 1.0 $\mu$g/kg | +40,25,36,24 | 31.3 ± 4.0 | +12,17,40,21 | 22.5 ± 6.1 |
| 2.0 $\mu$g/kg | +64,48,58,34 | 51.0 ± 6.6 | +28,30,66,31 | 38.8 ± 9.1 |
| 6.0 $\mu$g/kg | +84,92,122,74 | 93.0 ± 10.3 | +64,72,120,63 | 79.8 ± 13.4 |
| Study #2: Endotoxic Animals | | | | |
| 0.3 $\mu$g/kg | +2,0,4,2,3 | 2.2 ± 0.7 | +2,0,4,2,2 | 2.0 ± 0.6 |
| 1.0 $\mu$g/kg | +6,4,9,10,6 | 7.0 ± 1.1 | +8,6,16,9,6 | 9.0 ± 1.8 |
| 2.0 $\mu$g/kg | +12,10,24,12,10 | 13.6 ± 2.6 | +19,14,44,20,20 | 23.3 ± 5.3 |
| 6.0 $\mu$g/kg | +25,26,72,26,20 | 33.7 ± 9.6 | +36,46,78,44,38 | 48.5 ± 7.6 |

This example shows the effects of endotoxin and of arginase on mean systolic blood pressure response to phenylephrine in pithed rats. Endotoxin (15 mg/kg body weight) was given by intravenous injection 6 hrs before the experiment began; arginase (300 I.U./Min. for 20 min.) was given intravenously to each rat after the "Without Arginase" measurements were made.

Table 2 shows the maximum increase in blood pressure following the phenylephrine dose indicated for each rat ("Raw Data"); note that the data is in pairs since each rat was tested first without arginase (at 0.3, 1.0, 2.0 and 6.0 ug/kg phenylephrine, in sequence) and was then retested with phenylephrine in the same dose and sequence after arginase treatment. Thus, the first line of data in the Table shows that four control rats were each tested with 0.3 $\mu$g/kg of phenylephrine. The first control rat showed a blood pressure of 16 mm Hg without arginase, but only 4 mm Hg after arginase administration ("with arginase"). For the second, third and fourth rats, the blood pressure increments were 14, ephrine drops from 93.0±10.3 mm Hg (a pharmacologically useful pressor agent response) in control animals to 33.7±9.6 m/m Hg (a poor pressor agent response) in endotoxic animals, a difference in pressor response of 59.3 mm Hg. In contrast, at the same phenylephrine dose in animals given arginase (i.e., decreased serum arginine levels), the pressor response in control and endotoxic animals was 79.8±13.4 and 48.5±7.6, respectively, a difference of only 31.3 mm Hg. Thus, depletion of plasma arginine with arginase very significantly restores the "normal" (hypertensive) response to pressor drugs, such as phenylephrine.

The data herein thus demonstrates that hypotension may be controlled, particularly in endotoxic animals, by manipulating an animal's serum arginine concentration. As serum arginine levels may be controlled in part through an animal's nutrition as they are through arginase administration, the present data provides a mechanism whereby hypotension (low blood pressure) may be corrected by maintaining the animal on an essentially arginine-free nutritional regimen. As such, the presently disclosed technique may also be used to prevent the development of hypotension in a patient at risk in a combination therapy with a pressor agent or one of the nitric oxide inhibitors, such as NMA, NNA or NAA, or a combination thereof, as described herein.

EXAMPLE 3

IN VIVO EFFECTS OF NITRIC OXIDE INHIBITOR NAA ON IL-1 INDUCED HYPOTENSION

The present example is provided to demonstrate the utility of NAA ($N^\omega$-amino-L-arginine) and other nitrogen analogs for increasing blood pressure, most particularly in a cytokine-induced hypotensive animal.

Effect of NAA on IL-1-Induced Hypotension

As summarized in Table 3 and illustrated in FIG. 1, anesthetized dogs (n=4) given IL-1 (50 μg/kg) developed a progressive, moderately severe hypotension, with MAP decreasing from a baseline of 111±7 mm Hg to 80±2 mm Hg within about 3 hours. The IL-1-induced hypotension was rapidly reversed by the intravenous administration of a single bolus dose of NAA (20 mg/kg, 88 μmol/kg); MAP increased by 46±9 mm Hg (58%) to 125±8 mm Hg. In all cases, MAP following NAA administration was If significantly higher than the pre-IL-1 baseline MAP (average increase=14.3±7.7 mm. In control dogs not given IL-1, administration of NAA also increased PLAP above baseline; the average increase in MAP was 20.1±3.8 mm Hg, a value not significantly different from the increase above baseline observed in the dogs given IL-1 (p=0.254). Thus, whereas NAA had a much greater pressor effect in dogs previously made hypotensive by administration of IL-1, the final MAP achieved after NAA administration was similar in control and IL-1-treated dogs.

Figure 8:
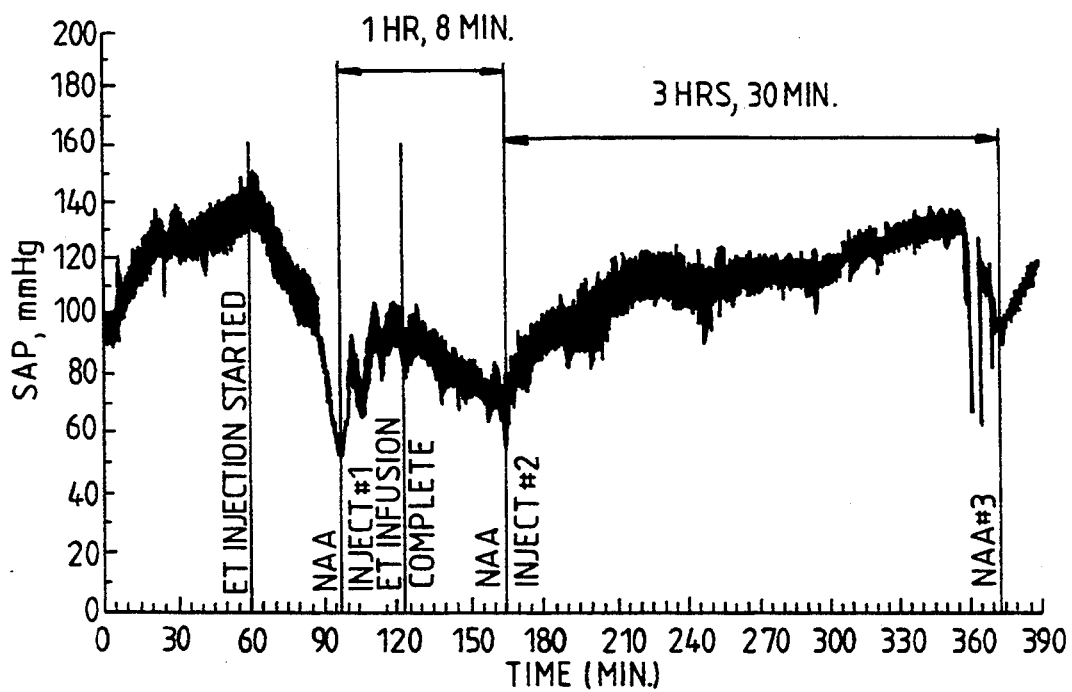
FIG. 8—Shows the reversal of endotoxin-induced systemic hypotension by N$^\omega$-aminoarginine (3 doses).

Specificity of the NAA pressor effect in both IL-1-treated and control dogs was demonstrated by its rapid and complete reversal by L-arginine (400 mg/kg, 2.3 mmol/kg); after arginine administration, MAP averaged 66±27 mm Hg in IL-1-treated dogs, but it was essentially at baseline levels in control dogs. In other studies with IL-1 and other cytokines (e.g., TNF and IL-2), the present inventors determined the duration of the NAA pressor effect in the absence of L-arginine. Single injections of NAA (20 mg/kg) in cytokine-treated dogs were found to maintain MAP at baseline or higher levels for up to about 60 minutes; second and third injections of NAA (20 mg/kg) had longer effects and maintained physiologically acceptable MAP readings for up to 7 hours (FIG. 8).

The central role of vasodilation in IL-1-mediated hypotension is exemplified by the observation that the decrease in MAP was associated with a 33.5% decrease in systemic vascular resistance (Table 3). Following administration of NAA, systemic vascular resistance increased in parallel with the restoration of MAP; systemic vascular resistance values after injection of NAA averaged 43% higher than baseline systemic vascular resistance measurements, although there was significant animal-to-animal variation. Following administration of arginine, systemic vascular resistance decreased substantially in all IL-1-treated animals (average decrease=61%). In control dogs, the NAA-mediated pressor effect was also associated with an increase in systemic vascular resistance.

Cardiac output was noted to decrease by 29.2% (P=0.046) in dogs treated with NAA alone. This decrease was completely reversed by the subsequent administration of L-arginine (Table 3). In dogs treated with IL-1, the cardiac output increased slightly, but not significantly (P=0.371). Administration of NAA caused a 25.2% reduction in cardiac output compared with that obtained after the administration of IL-1 (P=0.037); however, this value was not statistically different from the baseline cardiac output (1.93 versus 2.25 L/minute; P=0.204). These changes were reversed by administration of L-arginine (Table 3). None of the compounds administered caused a significant change in heart rate.

TABLE 3

| Nitric Oxide Synthase Inhibition in Rats | | | | |
|---|---|---|---|---|
| Dog | Mean arterial pressure, mm Hg | Heart rate, beats per minute | Cardiac output, L/min | Systemic vascular resistance, dynes-scc/cm$^5$ |
| Control (n = 3) | Baseline, 107.9 ± 28.1 | 113.5 ± 15 | 2.43 ± 0.88 | 3649 ± 651 |
|  | After NAA, 128.1 ± 29.5 | 94.3 ± 1 | 1.72 ± 0.74 | 6271 ± 1082 |
|  | After arginine, 119.1 ± 6.7 | 107.5 ± 22 | 2.35 ± 0.65 | 4116 ± 447 |
| IL-1-treated (n = 4) | Baseline, 111.1 ± 6.7 | 103.6 ± 16 | 2.25 ± 0.25 | 3747 ± 492 |
|  | After IL-1, 79.7 ± 1.5 | 102.1 ± 14 | 2.58 ± 0.70 | 2491 ± 756 |
|  | After NAA, 125.4 ± 8.4 | 97.1 ± 23 | 1.93 ± 0.48 | 5366 ± 1918 |
|  | After arginine, 66.0 ± 26.9 | 95.0 ± 15 | 2.20 ± 0.68 | 2087 ± 937 |

*Dogs were anesthetized and treated as described. Initial physiological parameters were monitored until constant (baseline). Control dogs were then given NAA (20 mg/kg) in a single bolus injection over 30 seconds. After MAP had stabilized for a least 20 minutes, L-arginine (400 mg/kg) was given. The IL-1-treated dogs were given IL-1 (50 μg/kg) intravenously for 3 minutes and were continuously monitored; the values shown as "After IL-1" represents readings taken at the nadir of MAP, just prior to administration of NAA. Blood pressure recovered within a few minutes of NAA administration; the values shown as "After NAA" represent readings made within 10 minutes of NAA injection. L-Arginine (400 mg/kg) was given for 5 minutes, and physiological determinations were made 10 minutes later. Data reported are mean ± s.d.

EXAMPLE 4

NMMA IN VIVO AND BLOCKAGE OF TNF-INDUCED HYPOTENSION

The present example is provided to demonstrate the in vivo utility of nitric oxide inhibitors, such as NMMA, for inhibiting hypotension. More specifically, the present example demonstrates that hypotension associated with the administration of TNF in the dog can be blocked by subsequent administration of NMMA. Furthermore, this increase in blood pressure in hypotensive animals is demonstrated to be reversible upon the administration of arginine. NMMA in its free base form has the structural formula:

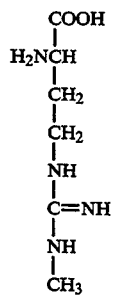

Furthermore, this inhibition of hypotension can be reversed by administration of an excess of arginine. These results show that NO• is the mediator of hypotension induced by TNF. Furthermore, activation of NO• synthesis may be involved in the pathogenesis of septic shock. This study also demonstrates the hypertensive action of arginine in a TNF-treated animal previously made normotensive by administration of NMMA.

Reagents

Recombinant human TNF, specific activity $2 \times 10^7$ units/mg, was from the Dainippon Chemical Corporation, Tokyo, Japan. TNF was administered at a dose of 10 μg//kg in a volume of 10 ml of phosphate buffered saline containing 17 mg/ml of dog albumin. NMMA was synthesized by adaptation of the method of Corbin and Reporter (Anal. Blochem. 57: 310–312, 1974), which reference is specifically incorporated herein by reference for this purpose. The NMMA was dissolved in 5 ml of phosphate-buffered saline for administration at a dose of 20 mg/kg. Arginine was obtained from Sigma Chemical Company, St. Louis, Mo.

Animals

Four conditioned mongrel dogs, 2 males and 2 females, weighing 28 to 30 kgs, were studied. Care of the animals were in accordance with the recommendations of the American Association for Accreditation of Laboratory Animals [DHEW(DHHS) publication no. (NIH) 78-23, revised, 1978]. On the day of the experiment, the dogs were fasted overnight. They were anesthetized with phenobarbital (25 mg/kg). The animals were then intubated orally with a #10 fr. endotracheal tube and ventilated with a Harvard pump ventilator at a rate of 14 breaths per minute and a tidal volume of 15 ml/kg. An arterial line was percutaneously placed in the femoral artery on the day of the experiment.

Physiological measurements

Mean (electronic) and phasic systemic arterial pressures (SAP) were continuously recorded on a Hewlett-Packard recording system (model 7758B) using strain gauge manometers (Hewlett-Packard model 1290A) which were connected to the arterial line. Heart rate (HR) was determined from an EKG tracing and continuously recorded on the Hewlett-Packard recording system. Oxyhemoglobin saturation (SaO₂) was obtained using a pulse oximeter (BIOX 111, Boulder, Col.). Continuous time-series records of SAP, HR, and SaO₂ were obtained using a Lab Master analog-to-digital convertor (16 channel, 12 bit, 30 kHz; Scientific Solutions, Inc.) sampling at 55 Hz and storing the 6 sec averages on a magnetic disk.

Figure 3:
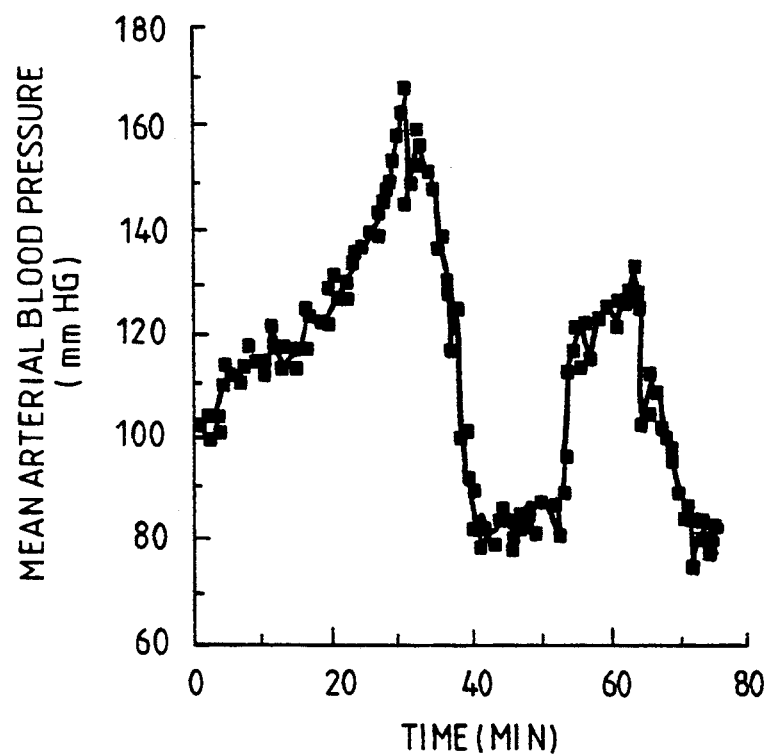
FIG. 3—Illustrates the effects of the sequential administration of NMMA and L-arginine on moderately low blood pressure of a dog treated with TNF.

NMMA was found to reverse the hypotension associated with the administration of TNF (FIG. 3). The pressor effect of NMMA occurred rapidly (within 2 minutes) and could be antagonized by administration of an excess of L-arginine. The antagonism of the NMMA pressor effect was stereospecific for the L-form of arginine.

Figure 4A:
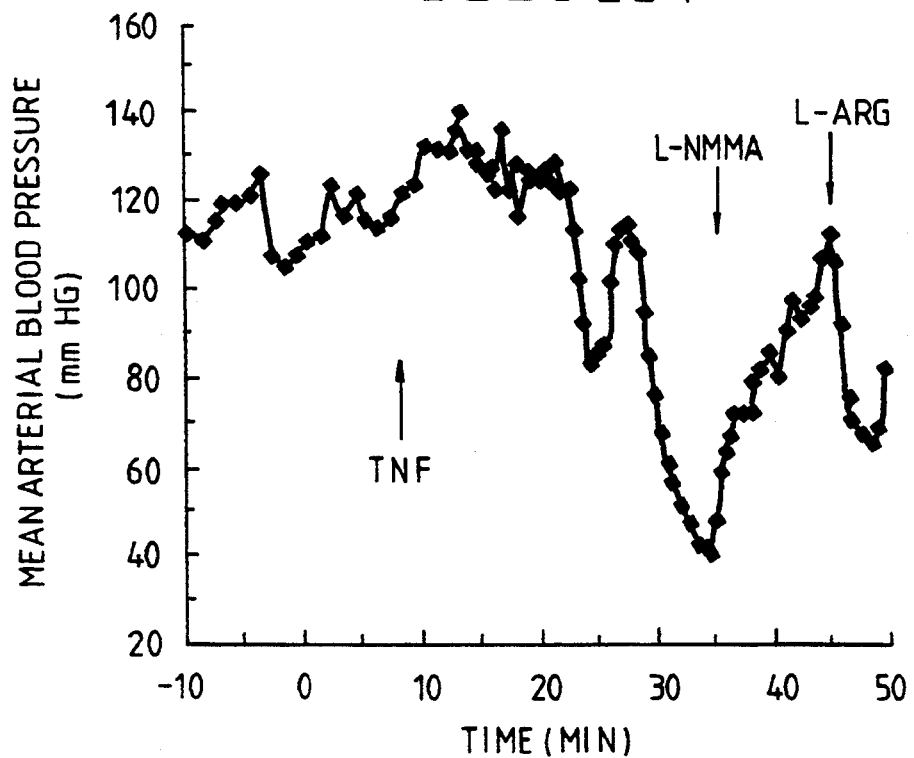
FIG. 4a—Illustrates the effects of sequential administration of NMMA and L-arginine on severe hypotension in a canine administered TNF.

The data shown in FIG. 3 is representative of several animal experiments. There were some variations noted in the degree of hypotension as well as the time of onset of hypotension after TNF administration. An example of severe hypotension resulting from administration of TNF is shown in FIG. 4a. Ten μg TNF/kg body weight was intravenously administered at the ten minute time point; 4.4 mg NMMA/kg at about 52 minutes; and 3 g Larginine at about 63 minutes. The onset of hypotension was found to occur between 30 to 60 minutes after TNF. The SAP dropped rapidly from 106 to 36. The administration of NMMA resulted in the rapid increase in blood pressure to an SAP of 116. This represents an 80 mm Hg increase in blood pressure after administration of NMMA.

Figure 4B:
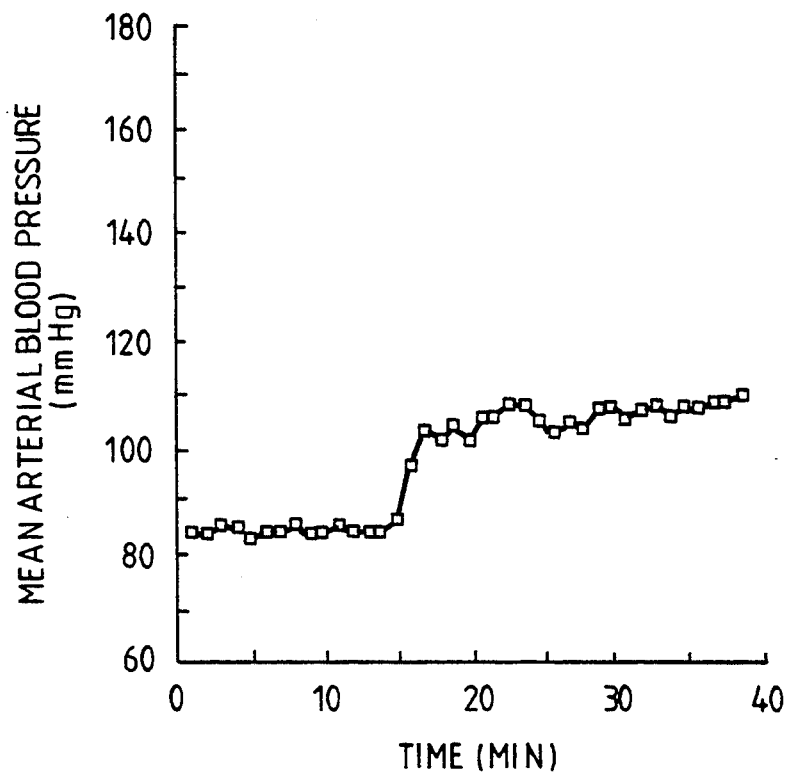
FIG. 4b—Illustrates control experiments where NMMA was administered to previously untreated dogs.
Figure 4C:
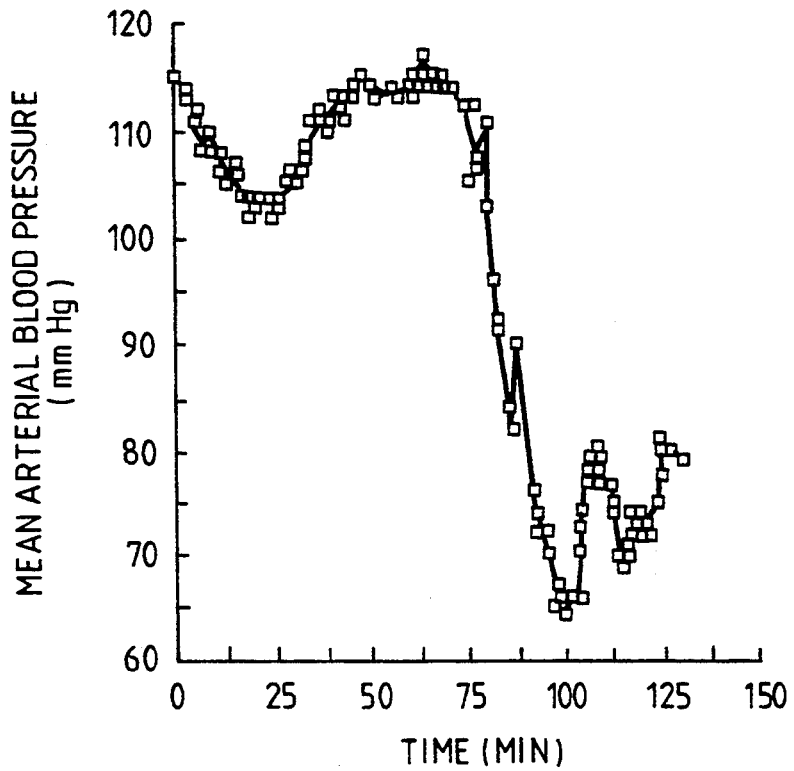
FIG. 4c—Illustrates the effects of NMMA on nitroglycerin-induced canine hypotension.

The administration of NMMA alone to untreated dogs (n=3) was also tested. Within 2 minutes after NMMA infusion, the blood pressure increased by 12 mm Hg. This was followed by a compensatory decrease in the HR with a return of the BP to baseline. The NMMA-induced bradycardia lasted 31 minutes. This response was not observed in animals which had been previously treated with TNF (FIG. 4b). Subsequent administration of L-arginine reversed these small changes observed in systemic arterial pressure. In a second control study nitroglycerin was infused at a rate of 28 μg/kg/minute, IV, to lower the blood pressure to the same level as that observed with tumor necrosis factor (FIG. 4c). After administration of NMMA in nitroglycerin infused dogs, the blood pressure increased only 14 mm. Subsequent administration of L-arginine reversed this modest effect.

The administration of L-arginine to cytokine treated dogs reversed the antihypotensive effects of NMMA. Blood pressure was not affected by the administration of L-arginine to previously untreated normotensive dogs.

The dose-limiting toxicity of TNF administered to patients is hypotension. These experiments support that proposition that NO•, also known as EDRF, is the mediator of the hypotension. Furthermore, these hemodynamic changes can be antagonized by an $N^\omega$-substituted arginine derivative and subsequently restored by the addition of excess arginine, supporting a role for arginine as the substrate for NO• synthesis. The present inventors have shown that NMMA can increase the resting blood pressure in the guinea pig. Therefore, NO• may play a role in normal arterial pressure homeostasis. This also appears to be true in the dog.

The pressor response to NMMA is much more dramatic in dogs with TNF-induced hypotension than in normotensive dogs. This suggests that TNF induced hypotension is due to an excess production of a vasoactive factor (i.e., NO•) which acts to regulate normal resting blood pressure.

TNF is also involved in the development of the toxicity observed in septic shock. Septic shock is most commonly caused by endotoxin, a component of the cell wall of Gram negative organisms. The administration of anti-TNF antibodies after TNF exposure does not protect against hypotension. However, administration of anti-TNF antibodies may protect against hypotension where administered before TNF exposure. This implies that endotoxin may induce other mediators of hypotension. The results presented herein indicate that NO• is the true mediator of that response.

EXAMPLE 5

L-NMA IN VIVO AND ENDOTOXIN-INDUCED HYPOTENSION

This example is provided to demonstrate the utility of nitric oxide synthase inhibitors, such as the arginine analog L-NMA, in treating hypotension in an animal.

In the present study, the effect of L-NMA on endotoxin-induced shock in dogs was examined. The present findings indicate that NO• is an important mediator of endotoxin-induced hypotension and that inhibitors of NO• synthesis should be of value in the treatment of septic shock.

Reagents

Nω-Methyl-L-arginine was synthesized as previously described by Corbin, et al.[56] (1974) (Nω-Methylated Arginines: Convenient Preparation of Nω-Methylarginines, *Anal. Biochem.*, 57, 310–312), which reference is specifically incorporated herein by reference for this purpose, and purified by crystallization as the monoflavianate salt. A solution of the free amino acid was obtained by stirring a suspension of the salt with Dowex-1 (OH); after neutralization with HCl, the concentration of L-NMA was determined by amino acid analysis using the crystalline monoflavianate salt as standard. Endotoxin (*Escherichia Coli*; B0128:B12) and all other reagents were purchased from Sigma Chemical Company, St. Louis, Mo. Nitroglycerin was purchased from DuPont Pharmaceuticals, Wilmington, Del.

Animals

Studies were carried out on 12 conditioned mongrel dogs (9 males and 3 females) weighing 22–32 kg (avg=25.3 kg). Animal care was in accordance with the recommendations of the American Association for Accreditation of Laboratory Animal Care, and met all standards prescribed by the Guide for the Care and Use of Laboratory Animals (Guide for the Care and Use of Laboratory Animals (1978) Dept. of Health, Education and Welfare, Washington, D.C. (Publ. No. 78-23). Animal protocols were approved by The University of Texas Animal Welfare Committee. The dogs were fasted overnight prior to the day of experimentation. They were anesthetized with sodium pentobarbital (25 mg/kg I.v.). Dogs were then endotracheally intubated and ventilated with a piston-driven respirator (Harvard instruments) using room air at a tidal volume of 15 ml/kg and at a rate of 12 to 14 breaths per minute, adjusted to achieve a normal arterial pH and $pCO_2$ (Instrumentation Laboratories 1L1302 pH/Blood Gas Analyzer). Catheters were placed percutaneously into the femoral and pulmonary arteries; In the latter, a flow-directed thermal-dilation catheter was used (Abbott Critical Care Systems).

Physiologic measurements

Mean SAP and heart rate were continuously monitored (Parametron 7048 Monitoring System, Roche) and stored on a magnetic disk using an analog-to-digital converter (Scientific Solutions, Inc.). Cardiac output (CO) was determined as the mean of six measurements by thermal-dilution. Systemic vascular resistance was calculated as (SAP X80)/CO and expressed as dynes-sec/$cm^5$.

Protocol

After the blood pressure and heart rate stabilized, endotoxin (40μg/kg, in 10 ml of phosphate-buffered saline (PBS), pH 7.4) was infused i.v. over 2 minutes. This dose of endotoxin typically induces severe and often lethal cardiovascular collapse in the dog. Blood pressure was monitored, and when either SAP fell below 60 mm Hg or a stable nadir in systemic arterial pressure (SAP) was maintained for 10 minutes, L-NMA was administered (20 mg/kg in 5 ml of PBS i.v. over 1 min.). In most experiments, L-arginine (400 mg/kg in 20 ml PBS) was administered ten minutes later by i.v. infusion over 2 minutes. In control experiments, dogs without prior exposure to endotoxin received L-NMA alone. To simulate the hypotension observed in dogs receiving endotoxin, one group of dogs received a continuous i.v. infusion of nitroglycerin (2 mg/ml) at a rate adjusted to maintain the SAP at 60–70 mm Hg. Nitroglycerin-treated dogs then received L-NMA (20 mg/kg) and 20 minutes later L-arginine was administered (400 mg/ml).

Statistics

Statistical significance was evaluated using Student's test and either a one-tailed or two-tailed analysis as appropriate for comparisons.

Figure 5:
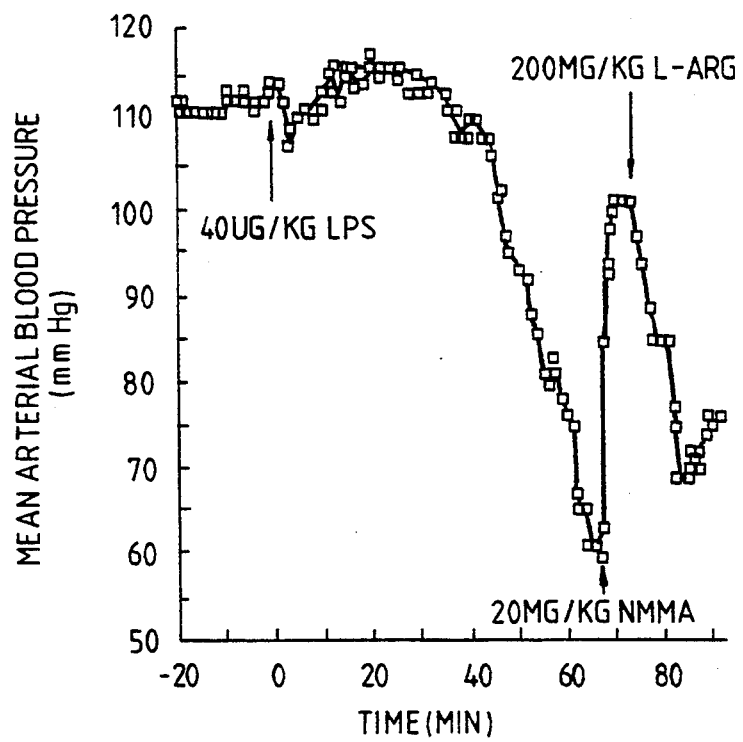
FIG. 5—Shows the time course of changes in mean systemic arterial pressure (SAP) in a pentobarbital-anesthetized dog following the IV administration of endotoxin (LPS; Lipopolysaccharide) (ET), N$^\omega$-methyl-L-arginine (L-NMA), and L-arginine (L-Arg).

A representative blood pressure tracing which depicts the effect of endotoxin on systemic arterial pressure in the anesthetized dog is shown in FIG. 5. Cardiovascular parameters for this and 3 additional dogs are summarized in Table 4.

TABLE 4

Hemodynamic Effects of L-NMA during Hypotension

| Type of Evaluation | Systemic Arterial Pressure (mmHg) | Heart Rate (beast/min) | Cardiac Output (L/min) | Systemic Vascular Resistance (dynes-sec/$cm^5$) |
|---|---|---|---|---|
| Study 1: Endotoxin-treated (n-4) | | | | |
| Baseline | 128.3 ± 9.4 | 119.5 ± 6.0 | 2.99 ± 0.32 | 3565 ± 454 |
| After Endotoxin | 59.5 ± 3.1** | 124.0 ± 7.6 | 2.17 ± 0.44 | 2403 ± 352 |
| After L-NMA | 107.3 ± 9.6** | 123.3 ± 4.8 | 2.03 ± 0.32 | 4462 ± 552** |
| After L-Arginine | 128.3 ± 9.4 | 119.5 ± 6.0 | 2.99 ± 0.32 | 3565 ± 454 |
| Study 2: Nitroglycerin-treated (n = 3) | | | | |
| Baseline | 129.3 ± 10.2 | 143.7 ± 12.1 | 3.14 ± 0.21 | 3294 ± 74 |
| During Nitroglycerin | 64.7 ± 2.7** | 137.3 ± 5.0 | 2.72 ± 0.27 | 1924 ± 132** |
| After L-NMA | 81.8 ± 3.5* | 191.7 ± 35.0 | 3.85 ± 0.80 | 1858 ± 399 |

TABLE 4-continued

Hemodynamic Effects of L-NMA during Hypotension

| Type of Evaluation | Systemic Arterial Pressure (mmHg) | Heart Rate (beast/min) | Cardiac Output (L/min) | Systemic Vascular Resistance (dynes-sec/cm$^5$) |
|---|---|---|---|---|
| After L-Arginine | 57.0 ± 13.0 | 148.7 ± 19.9 | 5.15 ± 1.08 | 1088 ± 491 |

For study 1, dogs were anesthetized, instrumented, and baseline cardiovascular measurements were recorded (Pretreatment). Endotoxin (40 ug/kg) was then administered and cardiovascular parameters were monitored. When blood pressure either reached a stable nadir or declined below 60 mm Hg (After endotoxin), L-NMA (20 mg/kg) was administered, and cardiovascular parameters were again determined (After L-NMA). After an additional ten min, L-arginine (400 mg/kg) was administered and cardiovascular measurements were determined 2 min. later (After L-Arginine). Results are reported as means ± S.E., (n = 4). Study 2 was carried out similarly, except that endotoxin was not administered. Instead, dogs received a continuous infusion of nitroglycerin (2 mg/ml) titrated to maintain SAP AT 65 mm Hg, (n = 3). Asterisks indicate statistically significant difference (*p < 0.005, **p < 0.001) from the immediately proceeding condition.

ET (40 μg/kg) produced a marked decrease in blood pressure within 120 min. (ΔSAP=−69±16 mm Hg, p<0.05). Untreated, this dose of endotoxin typically causes lethal cardiovascular collapse in the dog. L-NMA largely reversed the hypotension within 1.5 minutes, increasing SAP by 47.8±6.8 mm Hg (p<0.01) and SVR by 2060±338 dynes-sec/cm$^5$ (p<0.01); HR and CO were unchanged (Table 4). L-arginine reversed the effect of L-NMA and restored the endotoxin-induced hypotension, decreasing both SAP (p<0.0.01) and SVR (p<0.01) to values similar to those observed before administration of L-NMA. As illustrated in FIG. 5, after L-arginine, blood pressure decreased to similar levels compared to those observed prior to L-NMA administration. FIG. 5 shows the time course of changes in mean systemic arterial pressure (SAP) in a pentobarbital-anesthetized dog following the i.v. administration of endotoxin (ET), Nω-methyl-L-arginine (L-NMA), and L-arginine (L-Arg). Data from this and additional experiments are summarized in Table 4.

Figure 6:
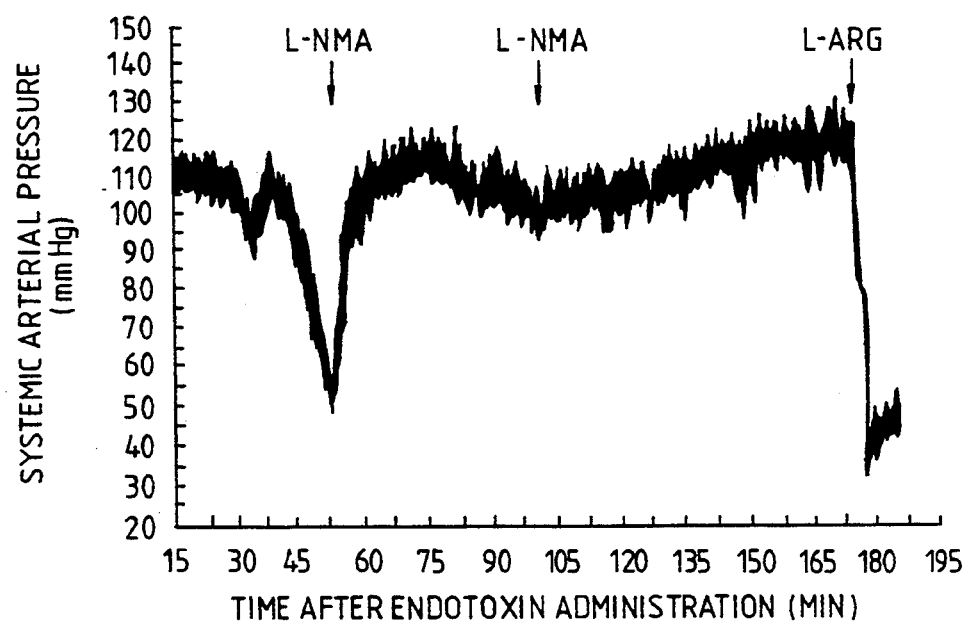
FIG. 6—Shows the time course of changes in mean systemic arterial pressure (SAP) in a pentobarbital-anesthetized dog following the i.v. administration of endotoxin, L-NMA (2 doses) and L-Arg.

In view of the potential clinical use of NO•-synthesis inhibitors in endotoxin- and cytokine-induced shock, it is important to establish that L-NMA can provide long-term reversal of hypotension. It was found that a single i.v. dose of L-NMA (20 mg/kg) restored normal blood pressure for 30-60 minutes. If an additional dose of L-NMA (20 mg/kg) was given when the blood pressure began to decrease again, normal blood pressure could be maintained for at least 2 hours in the endotoxin-treated dog. Results of a typical study are shown in FIG. 6. The maintenance of normal blood pressure continued to be dependent on L-NMA even after 2 hours since L-arginine could still restore endotoxic hypotension at this time (i.e., a decline in blood pressure to less than 45 mm Hg). FIG. 6 shows the time course of changes in mean systemic arterial pressure (SAP) in a pentobarbital-anesthetized dog following the i.v. administration of endotoxin. After 53 min. blood pressure declined to 47 mm Hg (ΔSAP=−61 mm Hg). Administration of L-NMA (20 mg/kg) resulted in a rapid reversal of the severe hypotension (73 mm Hg increase in SAP within 10 min). Blood pressure was maintained for 48 min by the first dose of L-NMA then started to decline. A second dose of L-NMA restored the blood pressure to a level equivalent to the first dose and maintained the SAP greater than 100 mm Hg for 2 hrs. To demonstrate than the potential for hypotension was still retained, the effect of L-NMA was reversed with an excess of L-arginine (400 mg/ml). This resulted in a decline in blood pressure to 43 mm Hg (ΔSAP=−77 mm Hg).

As shown in Table 5, L-NMA alone had a significant but modest hypertensive effect in control dogs not treated with endotoxin; L-NMA increased SAP by only 24.8±2.7 mm Hg (p,0.01) with an associated increase in SVR (p=0.01), and decreases in heart rate (HR) and cardiac output (CO) that did not reach statistical significance. L-arginine (400 mg/kg) fully reversed the pressor effect of L-NMA.

TABLE 5

HEMODYNAMIC EFFECTS OF L-NMA IN CONTROL DOGS

| | Systemic Arterial Pressure (mm Hg) | Heart Rate (beats/min) | Cardiac Output (L/min) | Systemic Vascular Resistance (dynes-sec/cm$^5$) |
|---|---|---|---|---|
| Baseline | 129.0 ± 10.9 | 121 ± 17.9 | 3.54 ± 0.68 | 3115 ± 347 |
| After L-NMA | 153.8 ± 11.4** | 82.5 ± 6.1 | 2.12 ± 0.26 | 5967 ± 523* |

Experiments were as described in FIG. 5, except that endotoxin was not administered. Results are reported as means ± S.E., (n = 4). Asterisks indicate significant differences from baseline (*p, 0.005, **p, 0.001). L-NMA = Nω-methyl-L-arginine.

In an additional series of experiments, blood pressure was reduced to 65 mm Hg by continuous i.v. infusion of nitroglycerin, a hypotensive agent that forms NO• by an L-arginine and NO• synthase-independent mechanism. Administration of L-NMA (20 mg/kg) to those dogs resulted in only a 17.1±5.0 mm Hg change without significant alteration in HR, CO, or SVR (Table 4).

The pathogenesis of the cardiovascular collapse that occurs during septic shock is poorly understood. Current treatment includes i.v. fluid administration and use of pressor drugs to increase peripheral vascular resistance and cardiac output. Very recently, endotoxin-binding agents including polymyxin B (Hanasawa, et al., 1989, New Approach to Endotoxic and Septic Shock by Means of Polymyxin B Immobilized Fiber Surg. Gynecol. Obstet. 168:232.) and antibodies which neutralize TNF (Tracey, et al., 1987, Anti-cachectin/TNF monoclonal antibodies prevent septic shock during lethal bacteremia Nature 330:662–664.) have been used in an attempt to modify the sequelae of septic shock. Although the latter approaches may have prophylactic value, there is not evidence that septic shock can be easily or rapidly reversed by removal of endotoxin or TNF.

Therapy of patients already in septic shock requires intervention at secondary and tertiary steps in the cascade of events initiated by endotoxin. Because the development of hypotension and other changes associated with septic shock may depend on complex interactions between cytokines, eicosanoids, PAF, activated complement components, and other factors, it is not surprising that several interventions have been found to be at least partially effective in some animal models.

Inhibitors of prostaglandin synthesis and PAF receptor antagonists are two major classes of compounds that may have therapeutic potential (8–9). Although these agents appear to be effective, they have been tested primarily in animals administered very large doses of endotoxin (e.g., 1 to 40 mg/kg, or about 1000 times larger than the dose used here). The onset of hypotension occurs within a few minutes in such animals and may not accurately reflect the cytokine-mediated processes characteristic of clinical septic shock.

In the present study with endotoxin and in a previous study with TNF (Kilbourn, et al. 1990, Nω-methyl-L-arginine inhibits tumor necrosis factor induced hypotension: Implications for the Involvement of Nitric Oxide, Proc. Natl. Acad. Sci., U.S.A. 87:3629), microgram doses of ET or TNF were administered, and the hypotensive response occurred after a delay of 30 to 90 min.

The present inventors demonstration (Kilbourn, et al. 1990, Nω-methyl-L-arginine inhibits tumor necrosis factor induced hypotension: implications for the involvement of NO•, Proc. Natl. Acad. Sci., U.S.A. 87:3629) that dogs given TNF exhibit a severe hypotension that can be substantially reversed by administration of L-NMA suggested that overproduction of NO• is a major factor in TNF-induced shock. The data in Table 4 show that L-NMA has a rapid and strong anti-hypotensive effect in the endotoxemic dog.

The effects of L-NMA on cardiac output and SVR in the four control dogs showed considerable variation. In two dogs, cardiac output decreased markedly ($\Delta \geq 1.5$ L/min.) and calculated SVR increased dramatically ($\Delta \geq 3500$ dynes-sec./cm$^5$). In contrast, major changes in cardiac output after L-NMA administration were not seen in any of the ET-treated dogs or in the other two control dogs; in the latter, SVR increased by only about 1400 dynes-sec./cm$^5$. Although these results suggest the possibility that L-NMA may have a direct effect on cardiac output under control conditions, additional studies are required. It is likely that activation of the arterial baroreceptor reflex mechanism accounts for the L-NMA-induced decrease in HR and CO under control conditions. In support of this view, it was observed that control dogs given phenylephrine at a dose that elevated SAP to a level similar to that produced by L-NMA alone also showed similar decreases in HR and CO. The lack of effect of L-NMA on HR or CO in hypotensive dogs may be because the level of hypotension was below the range of baroreceptor reflex sensitivity.

In view of the multiple mediators reported to contribute to septic shock, it was the expectation that even complete inhibition of NO• formation could not fully reverse the hypotension of ET-induced shock. Indeed, that blood pressure was not fully restored to pretreatment values by 20 mg/kg L-NMA suggests that mediators other than NO• contribute modestly to hypotension in the endotoxemic dog. The possibility that NO• synthesis was not fully inhibited by the administered dose of L-NMA provides an alternative explanation for the failure to fully restore blood pressure to pretreatment levels. Although direct determination of the extent of NO• synthesis inhibition is not possible in vivo, limited dose response studies indicate that L-NMA doses greater than 20 mg/kg do not have a significantly greater pressor effect. The ET-induced hypotension escaping blockade by 20 mg/kg L-NMA may be due to mediators other than NO•. While it may be that long-term inhibition by L-NMA may be self-limited by conversion to L-Arginine (Salvemini, et al., 1990, Immediate Release of a Nitric Oxide-Like Factor from Bovine Aortic Endothelial Cells by Escherichia coli Lipopolysaccharide. Proc. Natl. Acad. Sci. 87:2593.), such metabolism would not be expected to diminish the short-term pressor effect of L-NMA which is shown in FIG. 5. Nevertheless, the finding that L-NMA restores blood pressure to normal or near normal values indicates that overproduction of NO• is a major, and perhaps the major, cause of hypotension in endotoxic shock.

In one study, a single injection of L-NMA (20 mg/kg) was able to reverse endotoxin-elicited hypotension for 30 to 60 min. As shown in FIG. 6, normotension could be maintained for at least 2 hours by a subsequent dose of L-NMA. The long-term reversal of endotoxin-induced hypotension with L-NMA demonstrates the potential clinical utility of this agent. In conclusion, these results suggest that NO• synthesis inhibitors should be of considerable value in the treatment of septic shock. Since administration of arginine reverses the pressor effect of L-NMA (FIG. 5, FIG. 6), it is clear that high concentrations of plasma arginine antagonise and may completely abrogate the beneficial effects of L-NMA. L-NMA and related nitric oxide synthase inhibitors should therefore be particularly useful in hypotensive animals maintained at low plasma arginine levels such as with a low arginine dietary source (an arginine-free TPN).

EXAMPLE 6

NMMA AND NAA IN VIVO AND TNF CYTOTOXICITY

NMMA does not inhibit the anti-tumor activity of TNF and IL-2, in vitro. TNF bioactivity was measured by the cytotoxicity towards murine L929 cells, in vitro. Addition of NMMA or Nωaminoarginine did not alter the cytolytic effect of TNF towards tumor cells in vitro (Table 6).

TABLE 6

| Effects of NMMA on the Cytolytic Activity of rh-TNF Against Actinomycin D-Treated L929 Cells | |
|---|---|
| [NMMA] (mM) | TNF Activity (Units/ml) |
| 0 | 594.5 |
| 0.125 | 536.9 |
| 0.250 | 538.2 |
| 0.500 | 562.4 |
| 0.750 | 404.7 |
| 1.0 | 415.7 |

Similarly, NMMA did not alter either the proliferation phase or the lytic phase of human LAK cells exposed to IL-2, in vitro (Table 7).

TABLE 7

| Effects of NMMA on IL-2 Mediated Lymphokine Activated Killer Cell Activity in vitro | |
|---|---|
| [NMMA] (mM) | % Target Cell Lysis* |
| 0 | 66.1 ± 9.5 |
| 0.25 | 63.3 ± 11.8 |
| 0.5 | 67.7 ± 10.8 |
| 1.0 | 59.3 ± 7.5 |
| 2.0 | 75.1 ± 4.1 |

*% Lysis calculated from the % of release of radioactivity from $^{51}$Cr-labeled Raji Target cells minus spontaneous release. Effector cells were human blood lymphocytes cultured for 4 days in the presence of 40 U/ml of IL-2 (E:T = 80:1).

Aminoarginine is the most potent inhibitor of nitric oxide production reported thus far. Since NMMA is metabolized to citrulline which can subsequently serve as a precursor for arginine biosynthesis, other arginine analogs were tested for their ability to inhibit nitric oxide production (Table 8).

TABLE 8

Comparison of the $ED_{50}\%$* values of $N\omega$-Substituted Arginine Analogs

| Analog | $ED_{50}\%$ |
| --- | --- |
| NMMA | 336.7 |
| Aminoarginine | 109.5 |
| Nitro-L-Arginine | 2115 |
| Nitro-D-Arginine | >4500 |
| Nitro-L-Arginine benzyl ester | >1200 |
| Nitro-L-Arginine methyl ester | 1826 |
| Nitro-D-Arginine methyl ester | >4500 |

*$ED_{50}\%$ + The effective dose of drug that inhibited 50% of the nitrite production by murine endothelial cells exposed to Ganna-Interferon (100 U/ml) and TNF (500 U/ml) in vitro.

Figure 7:
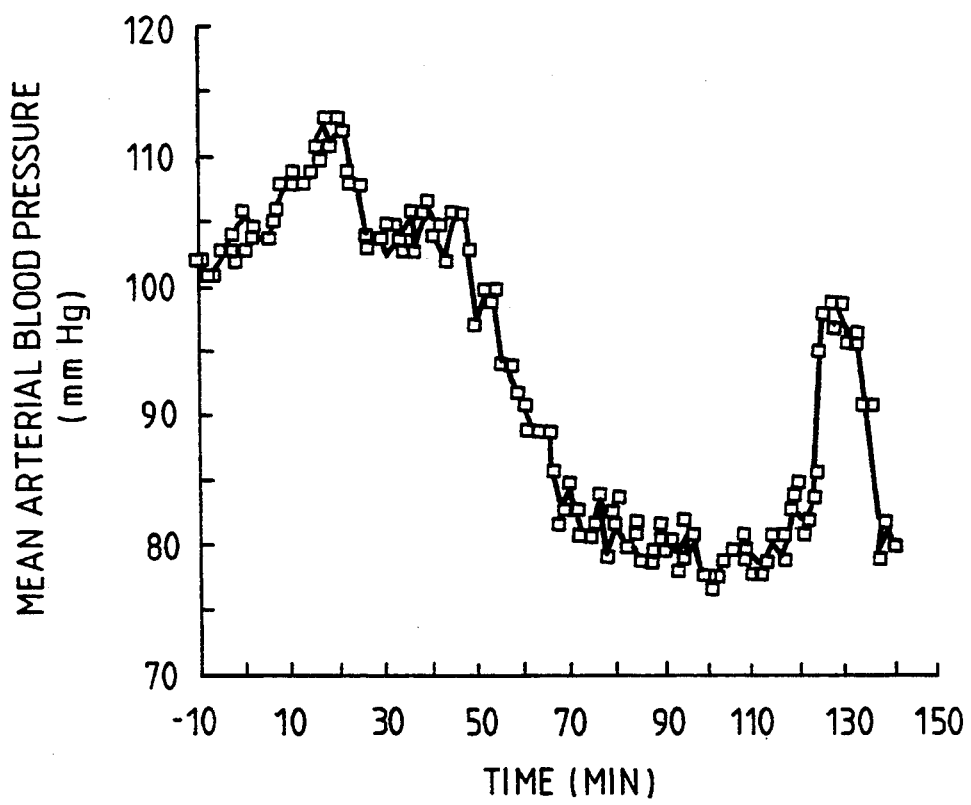
FIG. 7—Shows the time course of TNF-mediated canine systemic hypotension and reversal by N$\omega$-aminoarginine.

The most potent derivative tested was $N\omega$-aminoarginine. Subsequent testing in vivo, showed that aminoarginine was as effective as NMMA in reversing the hypotension associated with TNF administration in the dog (FIG. 7).

The reversal of ET shock (lethal dose) by $N\omega$-aminoarginine (NAA) for 4 hrs. 38 min. was demonstrated using multiple doses of aminoarginine (NAA). FIG. 8 depicts systemic arterial pressure (SAP) versus time (min). ET (2 mg/kg), a lethal dose, was infused over 60 min. and NAA administered at 97, 165, and 374 min. to maintain blood pressure. The animal was survived for 24 hours and then autopsied. No pathological changes were observed in liver, lungs, heart, brain, bowel or kidney.

EXAMPLE 7

ANTI-HYPOTENSIVE ARGININE-FREE TPN FORMULATION

The present example defines an anti-hypotensive TPN formulation of the present invention. This arginine-free formulation is intended to be used to reduce plasma arginine levels in an animal. The reduced arginine levels in the animal will then augment the anti-hypotensive effect of the nitric oxide synthase inhibitors described herein. This combination therapy can thus be used in the treatment of conditions where hypotension is the sole or an attendant symptom. For example, this regimen may be used in the treatment of an animal in septic shock, an animal treated with chemotherapeutic agents which may reduce blood pressure, or an animal which is generally experiencing hypotension due to trauma.

A sterile, non-pyrogenlc, stable solution for parenteral administration to a patient having hypotension or at risk of hypotension or systemic shock, particularly those receiving immunomodulatory agents, is prepared from pure crystalline amino acids, which are dissolved in a glucose solution (5% to 20%) in the following concentrations to provide a 2X concentrate TPN or a ready-to-feed TPN formulation, as indicated:

TABLE 9

| Amino Acids | 2x concentrate mg/100 ml formulation | Final Concentration (Feeding Formulation) g/l |
| --- | --- | --- |
| isoleucine | 600–800 | 3–4 |
| leucine | 800–1200 | 4–6 |
| valine | 600–800 | 3–4 |
| phenylalanine | 200–400 | 1–2 |
| methionine | 200–400 | 1–2 |
| lysine | 600–800 | 3–4 |
| histidine | 200–400 | 1–2 |
| threonine | 400–600 | 2–3 |
| tryptophan | 100–300 | 0.5–1.5 |
| tyrosine | 50–150 | 0.25–0.75 |
| alanine | 800–1000 | 4–5 |
| aspartic acid | 400–600 | 2–3 |
| glycine | 800–1000 | 4–5 |
| proline | 600–800 | 3–4 |
| serine | 200–400 | 1–2 |

To obtain the preferred TPN formulation concentration suitable as a feeding formulation, a volume of 500 ml of the 2X concentrate (defined in Table 9) is mixed with 500 ml of a 50% dextrose solution, for the production of 1 liter of the feeding formulation (i.e., 500 cc of a 2X concentrate of AA and 500 cc of dextrose solution). Most preferably, the dextrose solution is supplemented with a physiologically acceptable concentration of vitamins and minerals.

The TPN of the present methods may also include glutamic acid (400–600 mg/100 ml of a 2X conc., or 2–3 g/l in a final concentration) and/or taurine (50–100 mg/100 mls. of a 2-fold concentrate; 0.25–0.5 g/l final concentration).

The solution is then filter sterilized into appropriate containers for intravenous fluids. To prepare for administration, the volume is then brought to the desired feeding solution concentration with an equal volume of sterile glucose solution. The TPN as a ready to feed formulation is then to be kept cool. The solution may then be administered to a patient intravenously (IV). The pH of the TPN solution must also be adjusted to a physiologically acceptable pH, between 7.0 and 7.4. The formulation is arginine-free.

PROPHETIC EXAMPLE 8

FORMULATIONS AND METHODS FOR INHIBITING HYPOTENSION AND SEPTIC SHOCK

The present prophetic example provides methods whereby the particularly defined arginine-free formulations described herein may be used in the treatment of patients at risk of developing hypotension or septic shock, or whom may require parenteral nutritional support and are at risk of developing or who have already developed hypotension or septic shock.

The proposed formulations and proposed methods may be used most particularly useful in the clinical management of patients requiring total parenteral nutritional support and receiving immunomodulators. The term "immunomodulator" refers to such agents as interferon, interleukin-2, interleukin-1 and tumor necrosis factor as used in the description of the present invention.

Many of the class of substances recognized as immunomodulators are used as anti-cancer chemotherapeutic agents or immunorestorative agents in cancer patients receiving standard cytotixic drugs. Thus, it is envisioned that the presently described methods would be effective for the clinical management of patients being maintained on parenteral nutritional support and receiving chemotherapeutic agents with immunomodulatory action or immunorestorative action (eg., interleukin-1).

According to the present invention, a method for prophylaxis or treatment of systemic hypotension related to the elevated production of nitric oxide in an animal is provided comprising administering to the animal a non-hypotensive formulation which is arginine-free comprising a mixture of amino acids in a pharmaceutically acceptable diluent. The formulation is again to be essentially arginine-free.

The formulation is to be administered to the patient until a physiologically acceptable blood pressure in the animal is reached and maintained. For a human, a physiologically acceptable systolic blood pressure level is about 100 mm Hg.

More particularly, the method of the present invention includes an essentially arginine-free formulation comprising a mixture of amino acids. The formulation should be prepared so as to be physiologically suitable as an intravenous hyperalimentation (total parenteral nutrition) solution for patients requiring such solutions.

Stated as a range of concentrations for the most preferred mixture of amino acids, the formulation of the presently disclosed methods and specially tailored arginine-free formulations is defined in Table 10. Most preferably, the proposed concentrations to be included in such a formulation appear in Table 10.

TABLE 10
PREFERRED RANGES OF AMINO ACIDS IN NON-HYPOTENSIVE FORMULATIONS about 3-4 g/l isoleucine (0.3-0.4%);
about 4-6 g/l leucine(0.4-0.6%);
about 3-4 g/l lysine (0.3-0.4%);
about 1-2 g/l methionine (0.1-0.2%);
about 1-2 g/l phenylalanine (0.2-0.2%);
about 2-3 g/l threonine ( 0.2 -0.3 % );
about 0.5-1.5 g/l tryptophan (0.05-0.15%);
about 3-4 g/l valine (0.3-0.4%);
about 4-5 g/l alanine (0.4-0.5%);
about 1-2 g/l histidine (0.1-0.2%);
about 3-4 g/l proline (0.3-0.4%);
about 1-2 g/l serine (0.1-0.2%);
about 0.25-0.75 g/l tyrosine (0.025-0.075%);
about 4-5 g/l glycine (0.4-0.5%); and
about 2-3 g/l aspartic acid (0.2-0.3%).

The formulation may also include ornithine. Where ornithine is part of the particular formulation, it is to be included at a concentration of about 1-2 grams/l of the TPN feeding formulation (about 0.1-0.2% ornithine).

Where the formulation is a parenteral formulation, the mixture should be adjusted so as to be physiologically compatible for parenteral administration.

The described non-hypotensive parenteral nutritional formulations may alternatively include low concentrations of arginine found not to provide sufficient substrate for nitric oxide production in hypotensive animals. A low concentration of arginine for purposes of the present invention is defined as less than or equal to about 0.1% arginine in the feeding formulation ready to be administered to the patient. Most preferably, the formulation may include between about 0.01% to about 0.1% arginine.

An additional most preferred embodiment of the claimed invention is essentially arginine-free. In one particularly preferred embodiment of the essentially arginine-free formulation, the amino acids ornithine and citrulline are included. Ornithine and citrulline contribute to the urea cycle substrate requirements of the animal. Ornithine or citrulline, or both are to be considered optional components of the formulation. These additional ingredients are to be included to support nutritional requirements of the urea cycle. Where ornithine and citrulline are included in the formulation, the concentration of these ingredients most preferred comprise about 0.1-0.2% (or 1-2 g/l) ornithine and about 0.1% (or 1 g/l) citrulline.

TABLE 11

| Arginine-Free Formulation Mixture of Amino Acids | | |
|---|---|---|
| Amino Acid | 2X Concentrate (mg/100 ml) | Final Feeding Concentration (g/l) |
| Isoleucine | 600 | 3 |
| Leucine | 1,000 | 5 |
| Lysine | 1,000 | 5 |
| Methionine | 200 | 1 |
| Phenylalanine | 300 | 1.5 |
| Threonine | 400 | 2 |
| Tryptophan | 200 | 1 |
| Valine | 500 | 2.5 |
| Alanine | 900 | 4.5 |
| Histidine | 300 | 1.5 |
| Proline | 700 | 3.5 |
| Serine | 400 | 2.0 |
| Tyrosine | 450 | 2.0 |
| Glycine | 800 | 4.0 |
| Aspartic acid | 600 | 3 |
| Ornithine | 400 | 2 |

The ornithine content described for the formulation above may be omitted or it may be replaced with citrulline at a concentration of about 2 g/l. The amino acids concentrate (2×) is mixed with a pharmaceutically acceptable diluent, such as for example, a glucose solution in a proportion of 1 to 1 (1 part amino acid solution to 1 part of a dextrose solution). In addition, trace elements, vitamin supplements and essential salts ($Na^+$, $K^+$, $PO_4^{--}$, $Ca^{++}$, $Mg^{++}$) may be added.

The anti-hypotensive formulations as part of a method for treating or preventing hypotension may be administered as a parenteral nutritional formulation according to parenteral feeding methods well known to those of skill in the medical arts.

In practicing the claimed method, a physiological benchmark will be referred to in order to determine at what point the administration of the arginine-free formulation should be terminated. For example, the patient's systolic blood pressure level may be monitored so as to determine when the patient has reached a physiologically acceptable level (defined as about 100 mm Hg). A return to normal systolic pressure may then be used to indicate the point at which nitric oxide production was reduced, and the animal being treated had escaped risk of a greater reduction in peripheral vascular resistance or arterial blood pressure.

As generally defined according to the claimed method, hypotension (low blood pressure) is defined as an adult human systolic blood pressure level of less than about 100 mm Hg. A physiologically acceptable systolic blood pressure in an adult human is at least about 100 mm Hg systolic blood pressure.[40]

It has been observed that serum arginine levels increase upon the administration of a standard TPN formulation.[41] Therefore, by eliminating arginine as an ingredient in a TPN formulation, the inventors propose that serum arginine levels will be significantly reduced in patients receiving such an arginine-free TPN formulation as compared to similarly situated patients whom had instead been receiving a standard TPN solution. A standard TPN solution which includes greater than about 0.1% arginine would not be expected to constitute a hypotensive formulation within the meaning of the present invention.

PROPHETIC EXAMPLE 9

THERAPEUTIC REGIMEN OF ARGININE-FREE FORMULATIONS AND NITRIC OXIDE INHIBITORS FOR THE TREATMENT OF HYPOTENSION

The present prophetic example is provided to outline a proposed method for treating the hypotension attendant a variety of pathologies, such as septic shock, chemotherapy-related hypotension, etc., in an animal. Most particularly, the herein described methods are provided to outline those most preferred methods for treating hypotension in an animal, such as a human, with the herein described arginine-free parenteral formulations and arginine analogs. The arginine analogs described herein have also been shown by the present inventors to be nitric oxide inhibitors, most specifically nitric oxide synthase inhibitors. Therefore, these terms may be used interchangeably in the description of the present methods and regimens.

One of ordinary skill in the medical arts armed with the in vivo and in vitro results disclosed herein regarding the effect of lowered physiological arginine in an animal and the effects of various arginine analogs and nitric oxide synthase inhibitors, will be apprised of sufficient teaching to employ the herein described therapeutic regimens and methods to treat hypotension in a patient. Particular physiological guidelines for the adaptation of doses and physiologically compatible solutions for use in a patient may be obtained through reference to a variety of medical text books, including Remington's *Pharmaceutical Sciences* (1990) (Mack Publishing Company, Easton, Pa. 18042, (18th edition)). This reference text is specifically incorporated herein by reference for the purpose of providing physiological and/or pharmacological guidelines to be considered by the clinician in preparing physiologically compatible and non-toxic formulations in treating a hypotensive condition in a patient.

The present inventors have demonstrated that a decrease in the physiological levels of arginine in an animal, particularly in a hypotensive animal will enhance the pressor response to a pressor agent in the animal to provide an increase in blood pressure in vivo. In addition, the inventors have demonstrated herein that administration of a variety of arginine analogs, including NMA, NAA and NNA, provide an effective means of increasing blood pressure in hypotensive animals. This effect was demonstrated, even more specifically, in endotoxin-induced hypotensive animals. The studies presented in the present disclosure have also demonstrated that hypotensive animals which were not treated in any manner to reduce physiological arginine levels demonstrated a blunted response to blood pressure increasing agents (pressor agents). These studies, taken together, provide a reasonable scientific expectation that a combination therapeutic regimen which decreased physiological levels of arginine in a hypotensive animal, and which provided for the concurrent administration of a arginine analog capable of increasing blood pressure, or which provided for the administration of such an arginine analog subsequent to an effective decrease in physiological arginine levels, will provide an effective treatment for improving and/or eliminating a hypotensive condition in a patient. A reasonable correlation may be made between the results reported herein using laboratory animals and those responses which may be expected upon treatment of a human patient.

Accordingly, hypotension in a patient may be effectively treated by initially maintaining the patient on a supportive dietary source which is arginine-free. It is contemplated that reduced physiological concentrations of arginine may be obtained in a patient by maintaining the patient on an arginine-free parenteral formulation (TPN). Elimination of arginine from the parenteral formulation will function to decrease available arginine in the animal. As demonstrated in the examples provided herein, a decrease in available arginine levels in a hypotensive animal will function to enhance the response of the animal to a pressor agent. Most preferably, it is contemplated that a sufficiently lowered arginine concentration in the patient may be obtained after the patient has been maintained on the arginine-free parenteral formulation for at least 2-6 hours. The patient should be monitored by the attending physician for a decrease in arginine concentrations. An initial plasma or serum arginine level should be obtained as a baseline from which to gauge relative increases or decreases in physiological arginine levels. Most preferably, plasma or serum levels of arginine in the patient will be reduced to less than 4 $\mu$M arginine prior to the administration of an arginine analog to the patient. Lesser reductions in serum arginine will, however, be acceptable and even more preferred in the practice of the described method.

While results between patients will vary, it is contemplated that maintenance of a patient on an arginine-free parenteral formulation for at least 2-24 hours will reduce physiological arginine levels in the patient sufficiently to provide the enhanced presser response with the arginine analog described herein. As used in the present description, the terms arginine analog and nitric oxide inhibitor and nitric oxide synthase inhibitor are used interchangeably.

Upon the reduction of physiological arginine levels in the patient to an acceptable level (defined as between trace and one-half of the original concentration of arginine) an arginine analog, such as NMA, NAA, NNA, or a combination thereof is to be administered to the patient. Most preferably, the arginine analog is to be administered via an intravenous route in a single bolus dose. The arginine analog is to be prepared most preferably in a sterile saline solution at a concentration sufficient to provide the patient with a dose of the arginine analog of the between 0.1 mg/kg to about 100 mg/kg. Again, most preferably, the dose of the arginine analog most preferred for use in the herein described method is between about 10 mg/kg to about 30 mg/kg, or about 20 mg/kg.

The patient should be monitored for relative increases or decreases in blood pressure continuously at least once every hour during the treatment, and especially after administration of the arginine analog. The arginine analog of choice most preferred is NMA. Where no increase in blood pressure is obtained upon administration of the arginine analog, the dose of arginine analog should be increased and the increased dose provided to the patient in a subsequent treatment within 30 minutes of the initial arginine analog treatment.

Maintenance of a patient with normal blood pressure on an arginine-free parenteral formulation will not serve to further increase blood pressure to life threatening levels. Therefore, the patient, once having achieved normal physiological blood pressure levels, may be maintained on the formulation for as long as necessary as indicated by the attending physician. In this regard, the patient is provided a nutritionally supportive regimen which will not precipitate a return of dangerously low blood pressure levels.

The aforedescribed methods may be employed in the treatment of patients receiving chemotherapeutic agents linked to the development of hypotension, such as IL-1 and 2, or TNF in the treatment and/or support of patients having developed septic shock, or whom have been exposed to endotoxin or other cytokines. In addition, it is contemplated that the formulation may be employed as a nutritional support for trauma patients who are at statistically increased risk of developing hypotension.

In addition to the aforedescribed sequence of treatment, the arginine analog may alternatively be administered to the patient concurrently with initiation of the patient on the arginine-free parenteral formulation. The arginine analog is again to be administered as a separate dose, such as by a separate single bolus intravenous dose of at least 20 mg/kg.

Most particularly preferred uses of the arginine-free TPN formulations described herein include the uses thereof to reverse pressor hypo-responsibility. Arginine-free TPN may thus be used to reverse the ineffectiveness of L-adrenergic agents such as epinephrine or dopamine in septic patients. The use of the present invention as a method for enhancing the effect of such agents in patients with septic shock is thus a most particularly preferred aspect of the present invention.

Changes may be made in the following methods and formulations defined therein, without departing from the scope and spirit of the following claims.

BIBLIOGRAPHY

The following references, insomuch as they supplement details and even further define particular aspects of protocols presented in the present disclosure, are specifically incorporated herein by reference for such purposes as may be indicated herein.

1. Parrillo, J. E. (1989) *Textbook of Critical Care*, 2nd edition. Shoemaker, W. C., Ayres, S., Grenvik, A. et al., editors. Saunders Publishing Co., Philadelphia, Pa., pp. 1006.
2. Natanson, C., Eichenholz, P. W. and Danner, R. L. et al., (1989) J. Exp. Med. 169, 823.
3. Hesse, D. G., Tracey, J. J., Fond, Y., Manogue, K. R., Pallindino, M. A., Cerami, A., Shires, G. T. and Lowry, S. F. (1988) Surg. Gynecol. Obstet. 166, 147.
4. Etienne, A., Hecquet, F., Soulard, C., Touvay, C., Clostre, F. and Braquet, P. (1986) Pharmacol. Res. Commun. 18., 71.
5. Halushka, P., Reines, H., Barrow, S., Blair, I., Dollery, C. Rambo, W., Cook, J. and Wise, W. (1985) Crit. Care Med. 13, 451.
6. Smedegard, G., Cui, L. and Hugli, T. (1989) Am. J. Pathol. 135, 489.
7. Beutler, B., Milsark, I. W. and Cerami, A. C. (1985) Science 229, 869.
8. Casals-Stenzel, J. (1987) European J. Pharmacology 135, 117.
9. Wise, W. Halushka, P., Knapp, R. and Cook, J. (1985) Circ. Shock 17, 59.
10. Furchgott, R. F. and J. Zawadski V.: The Obligatory Role of Endothelial Cells in the Relaxation of Arterial Smooth Muscle by Acetylcholine. Nature 288:373–376, 1980.
11. Ignarro, L. J.: Biosynthesis and metabolism of endothelium-derived nitric oxide. Ann Rev Pharmacol. Toxicol 30:535–60, 1990.
12. Hibbs, J., and Taintor, R. (1986). Activated Macrophage-Mediated Cytotoxicity: Use of the in Vitro Cytotoxicity Assay for Study of Bioenergetic and Biochemical Changes That Develop in Tumor Target Cells. *Methods in Enzymology*, 132, 508–520.
13. Aisaka, K., S. Gross, O. Griffith and R. Levi: $N^G$-methylarginine, An Inhibitor Of Endothelium-Derived Nitric Oxide Synthesis, Is A Potent Pressor Agent In The Guinea Pig: Does Nitric Oxide Regulate Blood Pressure In Vivo? Blochem Biophys Res. Commun 160:881–886, 1989.
14. Rees, D., R. Palmer and S. Moncada: Role of endothelium-derived nitric oxide in the regulation of blood pressure. Proc Natl Acad Sci USA 86:3375–3378, 1989.
15. Sakuma, I., Stuehr, D., Gross, S., Nathan, C., and Levi R. (1988). Identification of arginine as a precursor of endothelium-derived relaxing factor. *Proc. Natl. Acad. Sci. USA*, 85, 8664–8667.
16. Fibbe, W. E., J. W. M. van der Meet, J. H. F. Falkenburg, M. S. Hamilton, P. M. Kluin and C. A. Dinarello: A Single Low Dose of Human Recombinant Interleukin-1 Accelerates the Recovery of Neutrophils in Mice with Cyclophosphamide-Induced Neutropenia. Exp Hematol 17:805–808, 1989.
17. Onozaki, K., K. Matsushima, B. Aggarwal and J. Oppenheim: Human Interleukin-1 is a Cytocidal Factor for Several Tumor Cell Lines. The Journal of Immunology 135:3962–3967, 1985.
18. Braunschweiger, P., C. Johnson, N. Kumar, V. Ord and P. Furmanski: Antitumor Effects of Recombinant Human Interleukin-1 alpha in RIF-1 and Panc02 Solid Tumors. Cancer Research 48:6011–6016, 1988.
19. Smith, J., W. Urba, R. Steis, J. Janik, J. Fenton, W. Sharfman, K. Conlon, M. Sznol, S. Creekmore, N. Wells, L. Elwood, J. Keller, K. Hestdal, C. Ewel, J. Rossio, W. Kopp, M. Shimuzu, J. Oppenheim and D. Longo: Interleukin-1 alpha: Results of a Phase 1 Toxicity and Immunomodulatory Trail. Am Soc Clin Oncol 9:717721, 1990.
20. Crown, J., A. Jakubowski, N. Kemeny, M. Gordon, C. Gasparetto, G. Wong, C. Sheridan, G. Toner, B. Meisenberg, J. Botet, J. Applewhite, S. Sinha, M. Moore, D. Kelsen, W. Buhles and J. Gabrilove: A Phase 1 Trial of Recombinant Human Interleukin-1B Alone and in Combination with Myelosuppressive Doses of 5-Fluorouracil in Patients with Gastrointestinal Malignancies. Blood (In press).
21. Steis, J., J. Smith II, R. Janik, R. Fenton, J. Sharfman, W. Rossio, W. Kopp, F. Buhles, J. Ruscetti, D. Keller, K. Longo, N. Hestdal, N. Wells and W. Urba: Phase 1 Study of IL-1 Beta (Syntex). Proc Am Soc Clin Oncol 10:211, 1991.
22. Dinarello, C., S. Okusawa and J. Gelfand: Interleukin-1 induces a shock-like state in rabbits: synergism with tumor necrosis factor and the effect of cyclooxygenase inhibition. Prog Clin Biol Res 286:243–263, 1989.

23. Calandra, T., J. Baumgartner, G. Grau, M. Wu, P. Lambert, J. Schellekens, J. Verhoef and M. Glauser: Prognostic Values of Tumor Necrosis Factor/Cachectin, Interleukin-1, Interferon-a, and Interferon-g in the Serum of Patients with Septic Shock. J Infect Dis 161:982-987, 1990.

24. Ohlsson, K., P. Bjork, M. Bergenfeldt, R. Hageman and R. Thompson: Interleukin-1 receptor antagonist reduces mortality from endotoxin shock. Nature 348:550-552, 1990.

25. Wakabayashi, G., J. A. Gelfand, J. F. Burke, R. C. Thompson and C. A. Dinarello: A Specific Receptor Antagonist for Interleukin-1 Prevents *Escherichia coli*-Induced Shock in Rabbits. FASEB J 5:338-343, 1991.

26. Kilbourn, R. G., S. S. Gross, A. Jubran, J. Adams, O. W. Griffith, R. Levi and R. F. Lodato: $N^\omega$-Methyl-L-Arginine Inhibits Tumor Necrosis Factor-Induced Hypotension: Implications for the Involvement of Nitric oxide. Proc Natl. Acad Sci USA 87:3629-32, 1990.

27. Stuehr, D. and O. W. Griffith: Mammalian Nitric Oxide Synthases. (Adv Enzymol In Press).

28. Levi, R., S. S. Gross, B. Lamparter, O. A. Fasehun, K. Aiska, E. A. Jaffe, O. W. Griffith and D. J. Stuehr. Evidence that L-arginine is the biosynthetic precursor of vascular and cardiac nitric oxide. In *Nitric Oxide from L-Arginine: A Bioregulatory System*, ed. S. Moncada and a. Higgs. 35-46. Amsterdam: Excerpta Medica, 1990.

29. Gross, S., D. Stuehr, K. Aisaka, E. Jaffe, R. Levi and O. Griffith: Macrophage And Endothelial Cell Nitric Oxide Synthesis: Cell-type Selective Inhibition By $N^G$-Aminoarginine, $N^G$-Nitroarginine And $N^G$-Methylarginine. Biochemical And Biophysical Research Communications 170:96-103, 1990.

30. Fukuto, J. M. K. S. Wood, R. E. Byrns and L. J. Ignarro: $N^G$-amino-L-arginine: a new potent antagonist of L-arginine-mediated endothelium-dependent relaxation. Biochem Biophys Res. Commun 168:458-65, 1990.

31. Fasehun, O., S. S. Gross, E. Pipili, E. A. Jaffe, O. W. Griffith and R. Levi: FASEB J 4:A309, 1990.

32. Gross, S. S., E. A. Jaffe, R. Levi and R. G. Kilbourn: Cytokine-Activated Endothelial Cells Express An Isotype of Nitric Oxide Synthase Which is Tetrahydrobiopterin-Dependent, Calmodulin-Independent and Inhibited by Arginine Analogs with a Rank Order of Potency Characteristic of Activated Macrophages. Biochem Biophys Res Commun 178:823-829, 1991.

33. Lambert, L. E., J. P. Whitten, B. M. Baron, H. C. Cheng, N. S. Doherty and I. A. Mcdonald: Nitric Oxide Synthesis in the CNS, Endothelium, and Macrophages Differs in its Sensitivity to Inhibition by Arginine Analogs. Life Sci 48:-69-75, 1991.

34. Nava, et al. (1991) Lancet 338:1555-1557.

35. Billar, et al. (1990) J. Leuk. Biol. 48:565-569.

36. Green, L., D. Wagner, J. Glogowski, P. Skipper, J. Wishnok and S. Tannenbaum: Analysis of Nitrate, Nitrite, and [$^{15}$N] Nitrate in Biological Fluids. Analytical Biochemistry 126:131-138, 1982.

37. Gross, S. S., Jaffe, E. A., Levi, R., and Kilbourn, R. G. (1991) Cytokine-Activated Endothelial Cells Express An Isotype of Nitric Oxide Synthase Which is Tetrahydrobiopterin-Dependent, Calmodulin-Independent and Inhibited by Arginine Analogs with a Rank Order of Potency Characteristic of Activated Macrophages. *Biochem. Biophys, Res. Commun.*, 178, 823-829.

What is claimed is:

1. A composition for the treatment of hypotension comprising a therapeutically effective amount of an arginine-free parenteral formulation, including a mixture of essential and non-essential amino acids, together in a pharmaceutically acceptable excipient; and a therapeutically effective amount of $N^\omega$-methyl-L-arginine capable of inhibiting nitric oxide production.

2. The composition of claim 1 wherein the $N^\omega$-methyl-L-arginine is at a concentration of between about 0.1 mg/kg and about 100 mg/kg.

3. The composition of claim 1 wherein the therapeutically effective amount of $N^\omega$-methyl-L-arginine is between about 10 mg/kg and 30 mg/kg.

4. The composition of claim 1 wherein the therapeutically effective amount of $N^\omega$-methyl-L-arginine is about 20 mg/kg.

5. The composition of claim 1 wherein the parenteral formulation includes a mixture of essential and non-essential amino acids defined as:

about 3-4 g/l isoleucine;
about 4-6 g/l leucine;
about 3-4 g/l lysine;
about 1-2 g/l methionine;
about 1-2 g/l phenylalanine;
about 2-3 g/l threonine;
about 0.5-1.5 g/l tryptophan;
about 3-4 g/l valine;
about 4-5 g/l alanine;
about 1-2 g/l histidine;
about 3-4 g/l proline;
about 1-2 g/l serine;
about 0.25-0.75 g/l tyrosine;
about 4-5 g/l glycine; and
2-3 g/l aspartic acid.

6. The composition of claim 1 wherein the parenteral formulation is about 1-2 g/l ornithine.

7. The composition of claim 1 wherein the parenteral formulation includes citrulline.

8. The composition of claim 1 wherein the parenteral formulation is prepared with a pharmacologically acceptable excipient defined as Ringers solution or saline.

9. The composition of claim 8 wherein the pharmacologically acceptable excipient is Ringers solution and the administration of the $N^\omega$-methyl-L-arginine follows administration of the parenteral formulation.

10. The composition of claim 1 wherein the pharmacologically acceptable excipient is saline.

11. The composition of claim 1 wherein the parenteral formulation includes ornithine at a concentration of about 1-2 g/l.

12. A method for treating hypotension in an animal comprising administering to said animal an effective amount of an anti-hypotensive formulation comprising an arginine-free mixture of essential and non-essential amino acids and a therapeutically effective amount of $N^\omega$-methyl-L arginine.

13. A method for treating chemotherapeutic agent related hypotension of an animal comprising administering to said animal an effective amount of a composition comprising an arginine-free mixture of essential and non-essential amino-acids and a therapeutically effective amount of $N^\omega$-methyl-L arginine.

14. A method for treating hypotension attendant to septic shock in an animal comprising administering to said animal an effective amount of a composition comprising an arginine-free mixture of essential and nonessential amino acids and a therapeutically effective amount of $N^\omega$-methyl-L arginine.

15. A method for providing nutritional support for an animal with or at risk of developing hypotension comprising:
   administering to the animal a nutritionally supportive amount of an arginine-free formulation of amino acids and administering a hypotension-inhibiting amount of $N^\omega$-methyl-L-arginine.

16. The method of claim 15 wherein the animal is a human.

17. The method of claim 15 wherein the $N^\omega$-methyl-L-arginine is administered intravenously.

18. The method of claim 15 wherein the arginine-free parenteral formulation comprises the following concentrations of essential and non-essential amino acids:
   about 3-4 g/l isoleucine;
   about 4-6 g/l leucine;
   about 3-4 g/l lysine;
   about 1-2 g/l methionine;
   about 1-2 g/l phenylalanine;
   about 2-3 g/l threonine;
   about 0.5-1.5 g/l tryptophan;
   about 3-4 g/l valine;
   about 4-5 g/l alanine;
   about 1-2 g/l histidine;
   about 3-4 g/l proline;
   about 1-2 g/l serine;
   about 0.25-0.75 g/l tyrosine;
   about 4-5 g/l glycine; and
   about 2-3 g/l aspartic acid,
   together in a pharmacologically acceptable excipient.

19. The method of claim 15 wherein the hypotensive inhibiting concentration of the $N^\omega$-methyl-L-arginine is between about 0.1 mg/kg and about 100 mg/kg.

20. The method of claim 15 wherein the hypotension inhibiting amount of $N^\omega$-methyl-L-arginine is between about 10 mg/kg and about 30 mg/kg.

21. The method of claim 15 wherein the parenteral formulation includes about 1-2 g/l ornithine.

22. The method of claim 15 wherein the parenteral formulation includes citrulline.

23. The method of claim 15 wherein the parenteral formulation includes ornithine and citrulline in an amount sufficient to maintain metabolic requirements of the urea cycle.

24. The method of claim 15 wherein the hypotension inhibiting amount of the $N^\omega$-methyl-L-arginine is about 20 mg/kg.

25. A method for treating chemotherapeutic agent-related hypotension comprising;
   monitoring an animal receiving a chemotherapeutic agent for a decrease in systolic blood pressure to less than about 100 mm Hg to detect an animal having systemic hypotension;
   treating the animal with an effective amount of a composition comprising an arginine-free parenteral formulation acids and a therapeutically effective amount of $N^\omega$-methyl-L-arginine;
   maintaining the animal on the composition and $N^\omega$-methyl-L-arginine until an increase of systolic blood pressure to at least about 100 mm Hg is detectable.

26. The method of claim 25 wherein the animal is a human.

27. The method of claim 25 wherein the chemotherapeutic agent is tumor necrosis factor, interleukin-2, interleukin-1, or a combination thereof.

28. The method of claim 25 wherein the arginine-free parenteral formulation comprises a mixture of essential and non-essential amino acids comprising:
   about 3-4 g/l isoleucine;
   about 4-6 g/l leucine;
   about 3-4 g/l lysine;
   about 1-2 g/l methionine;
   about 1-2 g/l phenylalanine;
   about 2-3 g/l threonine;
   about 0.5-1.5 g/l tryptophan;
   about 3-4 g/l valine;
   about 4-5 g/l alanine;
   about 1-2 g/l histidine;
   about 3-4 g/l proline;
   about 1-2 g/l serine;
   about 0.25-0.75 g/l tyrosine;
   about 4-5 g/l glycine; and
   about 2-3 g/l aspartic acid,
   together in a pharmacologically acceptable excipient.

29. The method of claim 25 wherein the therapeutically effective concentration of the $N^\omega$-methyl-L-arginine is between about 0.1 mg/kg to about 100 mg/kg.

30. The method of claim 25 wherein the arginine-free parenteral formulation includes ornithine at a concentration of about 1-2 g/l.

31. The method of claim 25 wherein the arginine-free parenteral formulation includes citrulline.

32. The method of claim 25 wherein the therapeutically effective concentration of $N^\omega$-methyl-L-arginine is about 10 mg/kg to about 30 mg/kg.

33. The method of claim 25 wherein the $N^\omega$-methyl-L-arginine is included at a therapeutically effective concentration of about 20 mg/kg.

34. A method for treating hypotension attendant to septic shock comprising:
   administering to an animal a therapeutically effective amount of an arginine-free parenteral formulation of amino acids and a therapeutically effective amount of $N^\omega$-methyl-L-arginine;
   maintaining the animal on the arginine-free parenteral formulation until a systolic blood pressure of at least 100 mm Hg is detectable in the animal.

35. The method of claim 34 wherein the septic shock is a bacterial endotoxin-related septic shock.

36. The method of claim 34 wherein the animal is a human.

37. The method of claim 34 wherein the therapeutically effective concentration of $N^\omega$-methyl-L-arginine is between about 15 mg/kg to about 30 mg/kg body weight of the animal.

38. The method of claim 34 wherein the therapeutically effective amount of the $N^\omega$-methyl-L-arginine is about 20 mg/kg body weight of the animal.

39. The method of claim 34 wherein the therapeutically effective amount of $N^\omega$-methyl-L-arginine is administered intravenously.

40. The method of claim 1 wherein the parenteral formulation is administered prior to the $N^\omega$-methyl-L-arginine in an amount sufficient to reduce plasma or serum concentrations of arginine.

41. A method for treating hypotension in an animal comprising:
   selecting an animal having a systolic blood pressure of less than about 100 mm Hg;

administering to said animal an effective amount of an anti-hypotensive formulation comprising an arginine-free mixture of essential and non-essential amino acids;

treating the animal with a therapeutically effective amount of $N^\omega$-methyl-L-arginine capable of inhibiting nitric oxide;

monitoring the blood pressure of said animal over a period of at least 24 hours; and maintaining the animal on the formulation and the $N^\omega$-methyl-L-arginine until a systolic blood pressure of at least about 100 mm Hg is detected.

42. The method of claim 41 wherein the animal is a human.

43. The method of claim 41 wherein the anti-hypotensive parenteral formulation comprises the following concentrations of essential and non-essential amino acids:

about 3–4 g/l isoleucine;
about 4–6 g/l leucine;
about 3–4 g/l lysine;
about 1–2 g/l methionine;
about 1–2 g/l phenylalanine;
about 2–3 g/l threonine;
about 0.5–1.5 g/l tryptophan;
about 3–4 g/l valine;
about 4–5 g/l alanine;
about 1–2 g/l histidine;
about 3–4 g/l proline;
about 1–2 g/l serine;
about 0.25–0.75 g/l tyrosine;
about 4–5 g/l glycine; and
about 2–3 g/l aspartic acid,
in a pharmaceutically acceptable excipient.

44. The method of claim 41 wherein the $N^\omega$-methyl-L-arginine is included at a therapeutically effective concentration of between about 0.1 mg/kg to about 100 mg/kg.

45. The method of claim 41 wherein the therapeutically effective concentration of $N^\omega$-methyl-L-arginine is between about 10 mg/kg to about 30 mg/kg.

46. The method of claim 41 wherein the therapeutically effective concentration of $N^\omega$-methyl-L-arginine is about 20 mg/kg.

* * * * *

UNITED STATES PATENT AND TRADEMARK OFFICE
CERTIFICATE OF CORRECTION

PATENT NO. : 5,374,651

DATED : December 20, 1994

INVENTOR(S) : Kilbourn et al.

It is certified that error appears in the above-indentified patent and that said Letters Patent is hereby corrected as shown below:

On the title page, item [54] and column 1, line 4, after "AND", insert --NOW--.

In claim 6, column 38, line 39, delete "is" and substitute therefor, --includes--.

In claim 8, column 38, line 43, delete "pharmacologically" and substitute therefor, --pharmaceutically--.

In claim 9, column 38, line 45, delete "8" and substitute therefor, --1--.

In claim 9, column 38, lines 45-47, delete "pharmacologically acceptable excipient is Ringers solution and the".

In claim 10, column 38, lines 49-50, delete "pharmacologically" and substitute therefor, --pharmaceutically--.

In claim 18, column 39, line 34, delete "pharmacologically" and substitute therefor, --pharmaceutically--.

In claim 21, column 39, line 41, delete "parenteral".

In claim 22, column 39, line 43, delete "parenteral".

UNITED STATES PATENT AND TRADEMARK OFFICE
CERTIFICATE OF CORRECTION

PATENT NO. : 5,374,651
DATED : December 20, 1994
INVENTOR(S) : Kilbourn et al.

It is certified that error appears in the above-indentified patent and that said Letters Patent is hereby corrected as shown below:

In claim 23, column 39, line 45, delete "parenteral".

In claim 25, column 39, line 61, immediately after 'formulation', insert --of amino--.

In claim 28, column 40, line 22, delete "pharmacologically" and substitute therefor, --pharmaceutically--.

In claim 40, column 40, line 61, delete "1" and substitute therefor, --34--.

Signed and Sealed this

Twenty-third Day of May, 1995

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,374,651

DATED : December 20, 1994

INVENTOR(S) : Kilbourn *et al.*

It is certified that error appears in the above-identified patent and that said Letters Patent is hereby corrected as shown below:

```
On the title page, item 54, line 3, immediately after 'AND',
insert --NON---.

On the title page, item 73, line 2, immediately after 'Tex.',
insert --Cornell Research Foundation, Inc., Ithaca, N.Y.--.
```

Signed and Sealed this

Twenty-ninth Day of February, 2000

Attest:

Q. TODD DICKINSON

*Attesting Officer*     *Commissioner of Patents and Trademarks*